United States Patent
Resnick et al.

(10) Patent No.: US 12,414,911 B2
(45) Date of Patent: Sep. 16, 2025

(54) TOPICAL COMPOSITIONS AND METHODS OF USE

(71) Applicant: MIRACLE FRUIT OIL, L.L.C., Miami Beach, FL (US)

(72) Inventors: Elizabeth Resnick, Miami Beach, FL (US); Lionel Resnick, Miami Beach, FL (US); Adam Resnick, Miami Beach, FL (US)

(73) Assignee: MIRACLE FRUIT OIL L.L.C., Miami Beach, FL (US)

( * ) Notice: Subject to any disclaimer, the term of this patent is extended or adjusted under 35 U.S.C. 154(b) by 416 days.

(21) Appl. No.: 15/229,406

(22) Filed: Aug. 5, 2016

(65) Prior Publication Data
US 2016/0361249 A1  Dec. 15, 2016

Related U.S. Application Data

(63) Continuation-in-part of application No. 14/024,898, filed on Sep. 12, 2013.

(60) Provisional application No. 61/700,981, filed on Sep. 14, 2012.

(51) Int. Cl.
| | |
|---|---|
| A61K 36/185 | (2006.01) |
| A61K 8/36 | (2006.01) |
| A61K 8/63 | (2006.01) |
| A61K 8/92 | (2006.01) |
| A61K 8/9789 | (2017.01) |
| A61K 9/00 | (2006.01) |
| A61K 31/20 | (2006.01) |
| A61K 31/201 | (2006.01) |
| A61K 31/575 | (2006.01) |
| A61Q 3/00 | (2006.01) |
| A61Q 5/00 | (2006.01) |
| A61Q 5/12 | (2006.01) |
| A61Q 17/00 | (2006.01) |
| A61Q 19/00 | (2006.01) |
| A61Q 19/08 | (2006.01) |

(52) U.S. Cl.
CPC .............. *A61K 8/922* (2013.01); *A61K 8/361* (2013.01); *A61K 8/63* (2013.01); *A61K 8/9789* (2017.08); *A61K 9/0014* (2013.01); *A61K 31/20* (2013.01); *A61K 31/201* (2013.01); *A61K 31/575* (2013.01); *A61K 36/185* (2013.01); *A61Q 3/00* (2013.01); *A61Q 5/006* (2013.01); *A61Q 5/12* (2013.01); *A61Q 17/005* (2013.01); *A61Q 19/00* (2013.01); *A61Q 19/004* (2013.01); *A61Q 19/007* (2013.01); *A61Q 19/08* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 6,117,119 | A | 9/2000 | Gould |
| 6,673,054 | B1 | 1/2004 | Gould et al. |
| 6,909,220 | B2 | 6/2005 | Chen |
| 2004/0037911 | A1 | 2/2004 | Letourneau et al. |
| 2007/0116766 | A1 | 5/2007 | Amick |
| 2008/0199533 | A1 | 8/2008 | DeLaRosa |
| 2010/0063008 | A1 | 3/2010 | Matteliano et al. |
| 2011/0121029 | A1 | 5/2011 | Pettingill |

FOREIGN PATENT DOCUMENTS

| | | |
|---|---|---|
| JP | 9-502196 A | 3/1997 |
| JP | 2001-122732 A | 5/2001 |
| JP | 2002316937 A | 10/2002 |
| JP | 2003-183210 A | 7/2003 |
| JP | 2003183120 A | 7/2003 |
| JP | 2005-298667 A | 10/2005 |
| JP | 2006265118 A | 10/2006 |
| WO | 2009067535 A1 | 5/2009 |

OTHER PUBLICATIONS

Raskin et al. (2004) Current Pharmaceutical Design, 10, 3419-3429. (Year: 2004).*
Medeiros et al. (2007) European Journal of Phamacology 559: 227-235. (Year: 2007).*
Inglett et al. (2011) Journal of Food Science, vol. 76: Nr. 3, C479-C482. (Year: 2011).*
Cheng et al. (2015) Int. J. Chem. Engineering and Applicatins, vol. 6, No. 3: 211-214. (Year: 2015).*
Gorin et al. (2017) Phytotherapy Res. 32: 321-332. (Year: 2017).*
He et al. (2016) Industrial Crops and Products, 86: 87-94. (Year: 2016).*
Office Action for Chinese Application No. 201380047613.4, dated Sep. 29, 2017.
Office Action for Australian Application No. 2013315536, dated Oct. 5, 2017.
Notice for Reasons for Rejection for Japanese Application No. 2015-532033, dated Sep. 6, 2016.

(Continued)

*Primary Examiner* — Russell G Fiebig
(74) *Attorney, Agent, or Firm* — Tarolli, Sundheim, Covell &Tummino LLP

(57) ABSTRACT

Compositions and methods of treatment are disclosed using compositions of extracts from the fruit of the *Synsepalum dulcificum* tree, which when applied topically in mammals, can provide benefit for dermatological and joint conditions. The extracts also contain anti-inflammatory, antimicrobial and spermicidal activity in vitro.

19 Claims, 6 Drawing Sheets

(56) References Cited

OTHER PUBLICATIONS

Chen C-Y et al., "The sour taste-modifying protein (miraculin), tyrosinase inhibitors and antioxidants from Synsepalum dulcificum", Current Nutrition & Food Science, Bentham Science Publishers, NL, vol. 5, No. 3, Aug. 1, 2009 (Aug. 1, 2009), pp. 172-179, XP009188452.
Kurihara Y, "Miracline compsn. used as sweetener—extracted from miracle fruit, contains saccharide(s) and specific sequence of 190 aminoacid(s)", WPI I Thomson, vol. 1991, No. 45, Sep. 25, 1991 (Sep. 25, 1991), XP002631623.
Extended European Search Report for Application No. 13837852. 6-1466/2895181 PCT/US2013059374 dated Mar. 2, 2016.
Thomas S.C.Li., "Vegetables and Fruits. Nutritional and Therapeutic Values", CRC Press, Taylor & Francis Group, 2008, p. 159.
P Jagadish Prasad, "Conceptual Pharmacology", Universities Press (India) Private Limited, 2010, p. 263.
International Search Report and Written Opinion, mailed Dec. 26, 2013.
Beattie, Julie, et al., "Potential Health Benefits of Berries", Current Nutrition & Food Science, 2005, 1, 71-86.
Boller, Shirley et al., "Anti-Inflammatory effect of Crude Extract and Isolated Compounds from Baccharis illinita DC in acute skin inflammation", Journal of Ethnopharmacology 130 (2010) 262-266.
Ching, Jianhong, et al., "Beta-Amyrin from Ardisia elliptica Thunb. is more potent than aspirin in inhibiting collagen-induce platelet aggregation", Indian Journal of Experimental Biology, vol. 48, Mar. 2010, pp. 275-279.
Cohen, Bernard, "The Cross-Section Trichometer: A New Device for Measuring Hair Quality, Hair Loss, and Hair Growth", Dermatol Surg, Jul. 7, 2008;34;900-911.
Evans, Trefor A., et al., "A Statistical analysis of hair breakage. II. Repeated grooming experiments", J. Cosmet. Sci., 61, 439-455, Nov./Dec. 2010.
Farafe, M.A., et al., "Evaluation of lotion formulations on irritation using the modified forearm-controlled application test method", Skin Research and Technology 2007, 13: 268-279.
Fregonesi, Andriana, et al., "Brazilian oils and butters: The effect of different fatty acid chain composition on human hair physiochemical properties", J. Cosmet. Sci., 60, 273-280 (Mar./Apr. 2009).
Garrido, Gabino, et al., In vivo and in vitro anti-inflammatory activity of Mangifera indica L. extract (Vimang®).
Guney, Sema, et al., Seed Lipids of the Miracle Fruit (*Synsepalum dulcificum*), Journal of Food Biochemistry 1 (1977) 173-184.
Inglett, George, E., "Contents of Phenolics and Flavonoids and Antioxidant Activities in Skin, Pulp, and Seeds of Miracle Fruit", Journal of Food Science, vol. 76, Nr. 3, 2011.
Kant, Ravi, "Sweet proteins—Potential replacement for artificial low calorie sweeteners", Nutrition Journal 2005, 4:5.
Leite, Sonia Pereira, et al., "Antimicrobial Activity of Indigofera suffruiticosa", Advance Access Publication, Apr. 5, 2006.
Mhaskar, Sudhakar, et al., "Hair Breakage index: An Alternative tool for damage assessment of human hair", J. Cosmet. Sci., 62, 203-207 (Mar./Apr. 2011).
Rendon, Marta, et al., "Treatment of melasma", J Am Acad Dermatol, vol. 54, No. 5, 2006.
S, Norshazila, et al., "Antioxidant Levels and Activities of Selected Seeds of Malaysian Tropical Fruits", Mal J. Nutr 16 (1) 149-159, 2010.
Snoussi, Ahmed, et al., "Improvement of the Composition of Tunisian Myrtle Berries (*Myrtus communis* L.) Alcohol Extracts", Journal of Agricultural and Food Chemistry, 2012, 60, 608-614.
Shao, Ling, et al., "Antibodies against outer-capsid proteins of grass carp reovirus expressed in *E. coli* are capable of neutralizing viral infectivity", Virology Journal 2011, 8:347.
Hormar, Halldor, et al., "Inactivation of Enveloped Viruses and Killing of Cells by Fatty Acids and Monoglycerides", Antimicrobial Agents and Chemotherapy, Jan. 1987, p. 27-31, vol. 31, No. 1.
Trookman, Nathan, S., et al., "Treatment of minor wounds from dermatologic procedures: A comparison of three topical wound care ointments using a laser wound model", J. Am Acad Dermatol, vol. 64, No. 3, Mar. 2011.
Wilken, Marlene K., et al., "Pilot Study of "Miracle Fruit" to improve Food Palatability for Patients Receiving Chemotherapy", Clinical Journal of Oncology Nursing, vol. 16, No. 5, Oct. 2012.
Zhou, Benhong, et al., "Spermicidal and Antigonococcal Effect of tannins from pomegranate rind", Journal of Medicinal Plants Research vol. 6(7), pp. 1334-1339, Feb. 23, 2012.
Boller et al. (2010) Journal of Ethnopharmacology 130: 262-266.
Finnin et al. (1999) Journal of Pharmaceutical Sciences, vol. 88, No. 10, 955-958.
He et al. (2016) Industrial Crops and Products 86: 87-94.
Williams et al. (2012) Advanced Drug Delivery Reviews 64: 128-137. Original Article:(2004) Advanced Drug Delivery Reviews, 56: 603-618.
Inglett et al. (2011) Journal of Food Science vol. 76, Nr. 3 C479-C482.
Rethinam et al. (2007) International Journal of Noni Research. vol. 2, Nos. 1-2, p. 1-34.
Website document entitled: "Pomegranate: the miracle fruit" (available at http://www.natureandhealth.com.au/news/pomegranate-the-miracle-fruit). Downloaded from website: Aug. 1, 2014.
Raskin et al. (2004) Current Pharmaceutical Design, 10, pp. 3419-3429.
Guney, et al., "Seed Lipids of the Miracle Fruit (*Synsepalum dulcificum*)", Journal of Food Biochemistry, 1977, 1, pp. 173-184.
Office action for Korean Patent Application No. 10-2015-7009646, dated Apr. 1, 2019.
Office action for Israeli Patent Application No. 237421, dated Oct. 4, 2018.
Chinese Office Action for Application No. 201380047613.4, Aug. 21, 2016.
Notice for Reasons for Rejection for Japanese Application No. 2015-532033, dated May 30, 2017.
Office action for Isreal Patent Application No. 237421, Dated Aug. 7, 2019.
Office action for India Patent Application No. 3069/DELNP/2015, dated Nov. 26, 2019.
Chinese Office action for Patent Application No. 201380047613.4, dated May 8, 2019.
Preliminary Office action for Brazilian Patent Application No. BR 11 2015 005339-4, dated Nov. 25, 2019.
Guney, S e Nawar, WW "Seed Lipids of the Miracle Fruit" Journal of Food Biochemistry, vol. 1, Apr. 1, 1977, pp. 173-184.
Kumar, et al., "Effect Of n-6 and n-3 Fatty Acids on the Prdlifeaation of Human Lymphocytes and Their Secretion of TNF 8 and IL-2 In Vitro", Nutrition Research, vol. 12, pp. 815-823, 1992.
Woo, et al., "Tumor Necrosis Factor-a Generates Reactive Oxygen Species via a Cytosolic Phospholipasc A2-linked Cascade", Biol. Chem., 2000, vol. 275, pp. 32357-32362.
Office action for Japanese Patent Application No. 2017-251250, dated Aug. 6, 2019.
Office action for Korean Patent Application No. 10-2015-7009646, dated Jul. 14, 2019.
Office action for Korean Patent Application No. 10-2019-7030044, dated Dec. 5, 2019.
Office action for Japanese Patent Application No. 2017-251250, Feb. 4, 2020.

* cited by examiner

TOPICAL COMPOSITIONS AND METHODS OF USE

RELATED APPLICATION

This application is a Continuation-in-Part of U.S. patent application Ser. No. 14/024,898, filed Sep. 12, 2013, which claims priority from U.S. Provisional Application No. 61/700,981, filed Sep. 14, 2012, the subject matter of which are incorporated herein by reference in their entirety.

FIELD OF INVENTION

This invention relates to compositions formulated for topical administration comprising an extract from the seed, skin, or pulp (flesh) of a berry of the plant, *Synsepalum dulcificum*, also known as miracle fruit, and methods for using the compositions in a mammal.

BACKGROUND

Berries contain micronutrients essential for health such as vitamin C, vitamin E, carotenoids, and folic acid. Furthermore, berries may have additional health benefits as they are also rich in phytochemicals, for example, containing phenolic compounds such as anthocyanins which are flavonoids responsible for their vivid red, violet, purple and blue colors (Norshazila S., Syed Zahir I., Mustapha Suleiman K. et al. Antioxidant Levels and Activities of Selected Seeds of Malaysian Tropical Fruits. Mal J Nutr. 2010 16(1): 149-159). In vitro studies indicate that anthocyanins and other polyphenols in berries have a range of potential health promoting properties including antioxidant, antimicrobial, anti-inflammatory, and anti-carcinogenic effects (Beattie J., Crozier A. and Duthie G G. Potential Health Benefits of Berries. Current Nutrition & Food Science. 2005 1: 71-86).

Berry extracts from various plant sources have been used in a variety of applications. Compositions comprising the berry extracts have been formulated for topical administration. For instance, U.S. Pat. No. 6,576,269 discloses the use of extracts of sea buckthorn in compositions for topical application on the skin to promote wound healing. In addition, U.S. Pat. No. 7,964,223 discloses blackberry extract compositions for treating inflammation and cancer. Furthermore, natural fruit oils from various berry seed sources have been used in a variety of topical applications. For instance, U.S. Pat. No. 5,916,573 discloses grape-seed oil for topical application on the skin. Similarly, U.S. Pat. No. 6,964,786 discloses *Momordica charantia* L. (bitter melon) oil compositions and their use as topical agents in the treatment of anti-inflammatory and anti-arthritic conditions.

The berry of the plant, *Synsepalum dulcificum*, is native to west tropical Africa, and has been known for centuries for its sweet-taste evoking properties (Kant R. Sweet proteins— potential replacement for artificial low calorie sweeteners. Nutr J. 2005 Feb. 9; 4:5. Review). It has been referred to as the tiny fruit that tricks the tongue by modifying its taste properties. The berry pulp contains a glycoprotein (Miraculin) that is able to alter the taste sensation by perceiving sweetness from sour flavors. Although the fruit berry has mainly been used in flavor tasting events and as a curiosity for a temporary alteration in the taste of certain foods or drinks, it has also been recommended for use by health practitioners to improve the dietary habits of patients with cancer and diabetes (Wilken M K and Satiroff B A. Pilot study of "miracle fruit" to improve food palatability for patients receiving chemotherapy. Clin J Oncol Nurs. 2012 October; 16 (5):E173-7).

The skin, and pulp (flesh), and seeds of the MFB contain phenolic and flavonoid compounds that exhibit antioxidant activity in vitro (Inglett G E. and Chen D. Contents of Phenolics and Flavonoids and Antioxidant Activities in Skin, Pulp, and Seeds of Miracle Fruit. Journal of Food Science. 2011 76(3): 479-482). The intense red-colored skin of the MFB contains a number of anthocyanin and flavonol pigments, such as cyaniding-3-monogalactoside, cyaniding-3-monoglucoside, cyanidin-3-monoarabinoside, delphinidin-3-monogalactoside, and delphinidin-3-monoaabinoside that have been isolated and found to contain antioxidant activity. The MFB pulp contains the Miraculin glycoprotein that provides the taste modifying properties associated with the fruit.

The seed, which constitutes the greater portion of the berry by weight, contains lipids (comprising approximately 10-15% of the dry weight of the seed) that have been previously characterized (Guney S. and Nawar W W. Seed Lipids of the Miracle Fruit (*Synsepalum dulcificum*). Journal of Food Biochemistry 1 (1977) 173-184). The fatty acid composition of the miracle fruit berry seed lipids comprises: palmitic acid (43% by wt.), oleic acid (32% by wt.), and linoleic acid (18% by wt.). As a result of the high level of saturated fatty acids, miracle fruit seed oil (MFSO) is a solid at room temperature. MFSO does not contain cholesterol.

The MFSO was found to be unique in its elevated content of α- and ß-amyrins, its major triterpene alcohols. These triterpene alcohols have previously been found to exhibit potent anti-inflammatory, anti-protease, and anti-aging effects (Ching J, Chua T K, Chin L C, Lau A J, Pang Y K, Jaya J M, Tan C H, Koh H L. Beta-amyrin from *Ardisia elliptica* Thunb. is more potent than aspirin in inhibiting collagen-induced platelet aggregation. Indian J Exp Biol. 2010 March; 48 (3):275-9).

In addition, MFSO contains a relatively high content of a phytosterol, identified as $\Delta^7$ spinasterol, which is not known to be present in other fruit oils. Phytosterols have been found to repair damaged tissue, acting as wound healing agents and also functioning to repair collagen and minimize wrinkling (Boller S, Soldi C, Marques M C, Santos E P, Cabrini D A, Pizzolatti M G, Zampronio A R, Otuki M F. Anti-inflammatory effect of crude extract and isolated compounds from *Baccharis illinita* DC in acute skin inflammation. J Ethnopharmacol. 2010 Jul. 20; 130 (2):262-6).

SUMMARY

The subject invention provides for the use of a composition, containing an extract of the MFB. The MFB extracts can be obtained from the seed, skin, or pulp and used individually or in combination in a composition for administration using any available or potential method of topical delivery system. For example, the MFSO is prepared by extraction from the fruit seeds of *Synsepalum dulcificum*. The skin or pulp are extracted from the seedless parts of the fruit.

The MFB extracts contain phenolic and flavonoid compounds, which impart anti-inflammatory and regenerative effects when used in a topical composition. Each of the MFB extracts has beneficial properties and unique ingredients that can be incorporated into compositions. For example, the MFSO extract composition comprises a unique mixture of palmitic acid, oleic acid, and linoleic acid. The MFSO composition can further comprise additional fatty acids and esters, triterpene alcohols, and phytosterols. It is believed that the MFSO composition described herein comprises a level of α- and ß-amyrins, its major triterpene alcohols, which is distinct from other fruit oils and advantageously provides potent anti-inflammatory, anti-protease, and anti-aging effects. Furthermore, MFSO contains a relatively high content of a unique phytosterol, identified as $\Delta^7$ spinasterol.

The composition is preferably administered topically and can further comprise a cosmetically or pharmaceutically acceptable carrier.

Further, the invention concerns the use of the MFB extract-based composition in the cosmetic care or treatment of skin, hair, nail, or mucous membrane, as well as the treatment of joint conditions in individuals. In addition, the topical administration of the MFSO or a composition or preparation comprising MFSO, is capable of enhancing the performance of skeletal joints by improving joint mobility, strength, stability, endurance and flexibility.

A further embodiment of the subject invention includes the use of the MFB seed, skin or pulp extract, or a composition or preparation comprising such extracts as an anti-inflammatory, or as an antimicrobial agent for a skin condition treatable with a composition comprising one or more of these properties, such as atopic dermatitis or psoriasis, seborrheic dermatitis including dandruff, acne, and rosacea.

The MFB seed, skin or pulp extract, or composition comprising such extracts can be used for moisturizing skin with improvement of skin conditions associated with excessive dryness or as a lubricant for sexual activity, as a skin protectant from irritants, in wound healing, or for treatment to minimize or reverse scarring.

As a cosmetic, the MFB seed, skin or pulp extract, or a composition or preparation comprising such extracts can be used as an anti-aging preparation, anti-wrinkle composition, or as a skin whitener. MFSO is also advantageously useful to improve or increase the sun-protecting action of sunscreen. The uses of the MFB seed, skin or pulp extract, or a composition comprising such extracts for hair care include hair softening with increasing shine, preventing hair breakage with enhanced hair conditioning, and reducing split-ends.

The uses of the MFB seed, skin or pulp extract, or a composition comprising such extracts for nails include moisturizer and lubricant for brittle nails.

The uses of the MFSO or a composition comprising the MFSO for skeletal joints include the improvement of joint mobility, strength, steadiness, endurance, flexibility and range of motion due to enhanced lubrication and a reduction of joint aches. In addition, the MFSO can be used for its skin-lubricating properties, and has further been determined to have spermicidal activity; therefore, MFSO, or a composition comprising MFSO can be used as a lubricant, a spermicide, or a spermicidal lubricant during sex.

Thus, it is an object of this invention to use a seed, skin, and pulp extract from the MFB; the lipid extract obtained from the seeds of the fruits of the *Synsepalum dulcificum* plant. Preferably, the skin, pulp, and the MFSO extract can be useful as a topically administered composition for the care or treatment of the skin, hair, nails, mucous membranes and/or appendages of the skin and joints.

It is another object of the invention to provide a topical composition in a stable form containing the skin and pulp from the MFB and the MFSO extracted from the seeds of *Synsepalum dulcificum*.

Yet another object of the present invention is to provide a composition comprising the skin and pulp from the MFB and the MFSO from *Synsepalum dulcificum* seeds mixed with any suitable cosmetically or pharmaceutically acceptable additives/carriers.

Still another object of the present invention is to provide a method for use of the skin and pulp from the MFB and the MFSO, alone or combined with other ingredients, in the cosmetic care or pharmacological treatment of dermatologic conditions affecting skin, hair, nail, and mucous membranes in individuals.

Still another object of the present invention is to provide a method for use of the MFSO, alone or combined with other ingredients, for improving a joint disorder or disease or to enhance joint mobility, strength, steadiness, endurance, flexibility, and range of motion or reduce joint fatigue in individuals.

In still another aspect, this invention provides for a skin and pulp extract from the MFB and a novel MFSO extract that, itself can be used in nutritional, cosmetic, personal care, pet care, aquaculture and pharmaceutical or healthcare products.

The subject invention comprises a topical pharmaceutical or cosmetic composition comprising a lipid-component extract from miracle fruit seed as an active ingredient in the composition. The extract includes about 43 wt. % to about 46 wt. % palmitic acid, about 32 wt. % to about 34 wt. % oleic acid, and about 18 wt. % to about 21 wt. % linoleic acid. The extract can further include about 5 wt. % to about 7 wt. % stearic acid and about 1 wt. % to about 2 wt. % myristic acid. The extract may further comprise at least one hydrocarbon, triterpene alcohol, low MW alcohol, or sterol.

A cosmetic composition of the subject invention can be formulated for topical application to treat, prevent or ameliorate a condition or disorder affecting skin, mucous membrane, hair or nails wherein the composition comprises a skin or pulp extract from the MFB or a lipid-component extract from miracle fruit seed as an active ingredient of said composition, and a cosmetically acceptable carrier.

A pharmaceutical composition of the subject invention can be formulated for topical application to treat, prevent, or ameliorate a condition or disorder affecting skin, hair, nail, mucous membrane or joint (e.g., carpal tunnel syndrome), wherein the composition comprises a skin or pulp extract from the MFB or a lipid-component extract from miracle fruit seed as an active ingredient of said composition, and a pharmaceutically acceptable carrier.

The composition of the invention advantageously comprises at least one property selected from, anti-inflammatory, antimicrobial, regenerative and performance-enhancing activity. The antimicrobial property is antibacterial, antiviral, or can be antifungal.

The subject invention also comprises a method for treating, preventing or ameliorating a condition or disorder affecting skin, mucous membrane, hair, or nail of an animal, wherein the method comprises: providing a composition of the invention; and topically applying an effective amount of said composition to the animal to prevent, ameliorate, improve or reverse said condition or disorder.

The condition or disorder treated, prevented or ameliorated by application of a composition of the invention may be dryness or brittleness of the hair, skin, mucous membrane or nail. The composition can be applied to the hair to moisturize or condition, reduce damage or brittleness due to dryness, or treat split ends of the hair.

The method of the invention can also comprise application to the skin, and can be useful for minimizing wrinkles or aging, or can treat undesired pigmentation, such as Melasma, wherein application of the composition results in skin whitening.

The method of the invention can also include application to the skin to moisturize dry or damaged skin, or may be a lubricant which can protect the skin from irritation by physical or chemical irritants.

The composition of the invention can also be used in a method for treating a condition of disorder caused by or associated with inflammation, the method comprising: providing a composition comprising the skin or pulp extract from the MFB or MFSO; and topically applying an effective amount of the composition to an area of a body to be treated to prevent, ameliorate, improve or reverse said condition or disorder caused by inflammation.

The inflammation can be external or may be internal, such as in a joint of the body. External inflammation treatable by application of a composition of the invention includes atopic dermatitis or psoriasis. Alternatively, the inflammation may be caused by or associated with bacteria, such as acne, rosacea, or a fungus, such as seborrheic dermatitis, including seborrheic dermatitis with dandruff, or a virus, such as herpes virus infection.

The method of the invention can also be used for regenerative activity by improving the healing of a wound, and can further reduce scarring.

The method of the invention can also be used for enhancing the performance of skeletal joint activity by improving the joint mobility, strength, steadiness, endurance, flexibility, and range of motion or by reducing joint fatigue in individuals.

A further method of the invention includes the use of a composition comprising MFSO in a sunscreen composition, and can be used in conjunction with a conventional sunblock ingredient to enhance the sun-block activity of the conventional sunblock or to prevent skin damage caused by UV-radiation caused by sun exposure.

The composition and method of the invention includes the use of a composition comprising MFSO as a sexual aid for its lubricating or spermicidal property.

The above uses, as well as other uses readily understood by a person of ordinary skill in the art, will be apparent form the description, including the accompanying drawings, as provided herein.

Other embodiments described herein relate to a method for treating, preventing or ameliorating a condition or disorder affecting hair, skin, nail, joint, muscle, or mucous membrane, or caused by or associated with inflammation of an animal in need thereof. The method includes administering miracle fruit seed oil and/or a composition comprising miracle fruit seed oil to the animal at an amount effective to treat the condition or disorder.

In some embodiments, the condition or disorder is dryness, weathering, or brittleness of hair, skin, nail, or mucous membrane.

In other embodiments, the miracle fruit seed oil and/or composition can applied to hair, and the condition or disorder is dull, frizzed, frayed, frazzled, or tangled hair, or split ends of the hair, or breakage of the hair due to a physical, chemical, environmental, or nutritional modality affecting the hair.

In some embodiments, the miracle fruit seed oil and/or composition is applied to the skin. The condition or disorder can be wrinkles or aging. The condition or disorder can also be undesired pigmentation, and the application of the miracle fruit seed oil and/or composition can result in skin whitening.

In other embodiments, the condition or disorder can be dryness of the skin. The application of the miracle fruit seed oil and/or composition to the skin can moisturize the skin, lubricate the skin, and/or protect the skin from irritation.

In some embodiments, the condition or disorder is skin damage caused by UV-radiation.

In other embodiments, the condition or disorder is atopic dermatitis, psoriasis, acne, rosacea, seborrheic dermatitis, or seborrheic dermatitis with dandruff.

In some embodiments, the inflammation is caused by or associated with a microbe.

In some embodiments, the condition is a wound or scar.

In other embodiments, the condition or disorder comprises at least one of stiffness, ache, or pain of the joint.

In still other embodiments, the condition is carpal tunnel syndrome.

In some embodiments, the miracle fruit seed oil and/or composition is applied to a joint of the animal at an amount effective to improve at least one of joint mobility, dexterity, strength, stability, endurance or flexibility.

In other embodiments, the miracle fruit seed oil and/or composition is applied to a muscle of the animal at an amount effective to improve at least one of muscle weakness and fatigue.

In some embodiments, the miracle fruit seed oil and/or composition is applied to skin or mucous membrane of the animal at an amount effective to kill sperm.

In some embodiments, the composition includes at least one of a pharmaceutically or cosmetically acceptable additive, excipient, or carrier that is exogenous to miracle fruit and facilitates topical delivery of the oil.

In some embodiments, the oil is extracted from seed of the miracle fruit berry by cold or hot pressed, solvent, or supercritical fluid extraction.

In other embodiments, the composition is in the form of a lotion, gel, liquid, oil, foam, paste, spray, cream, ointment, powder, suppository, troche, patch, strip, film, or emulsion.

In some embodiments, the oil can include about 43 wt. % to about 46 wt. % palmitic acid, about 32 wt. % to about 34 wt. % oleic acid, and about 18 wt. % to about 21 wt. % linoleic acid. The oil can further include about 5 wt. % to about 7 wt. % stearic acid and about 1 wt. % to about 2 wt. % myristic acid. The oil can further include at least one hydrocarbon, triterpene alcohol, low molecular weight alcohol, or sterol.

In some embodiments, the composition can include about 0.01 wt. % to about 99.99 wt. % of the oil.

BRIEF DESCRIPTION OF THE DRAWINGS

An understanding of the invention is readily made by the description herein, embodiments of which are illustrated by the accompanying drawings, in which.

DETAILED DESCRIPTION

Figure 1:
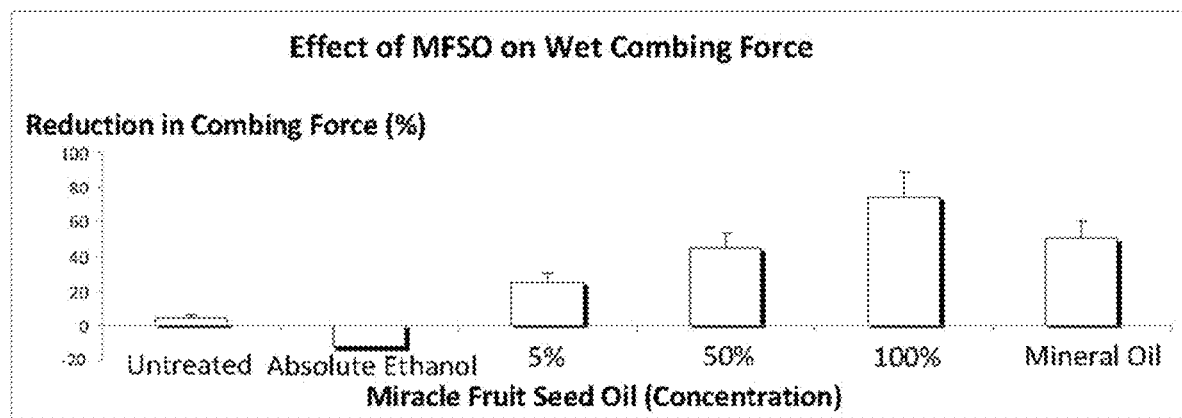
FIG. 1 is a graph illustrating that MFSO reduces the wet combing force on hair tresses in vitro.

A "composition" as used herein refers to as a mixture containing the seed (MFSO), skin or pulp extract, and can include a preparation using the seed (MFSO), skin or pulp extract in conjunction with at least one carrier. The composition may also contain one or more additional agents including emulsifiers, alcohol, water, emollients, humectants, dry-feel modifiers, antimicrobial preservatives, thickening agents, antifoaming agents, chelating agents, and fragrances as well as any other class of materials whose presence may be pharmaceutically, cosmetically, or efficaciously desirable. The terms "solution", "preparation", "emulsion" and "composition" are used interchangeably herein. The compositions of the present invention include lotions, creams, beach oils, gels, sticks, sprays, ointments, balms, serums, pastes, mousses, drops, foams, collodions, suspensions, powders, aerosols, cosmetics and liquids.

The terms "administer" or "administering" as used herein are defined as the process by which the compositions of the present invention are delivered to the individual for treatment purposes or to enhance performance. Topical administration can involve the use of vesicular concept delivery systems, such as liposomes, niosomes, transferosomes, etc., and transdermal administration, such as transdermal patches, strips, films, or the like. In addition, other physical methods of topical delivery systems and devices may be used, such as iontophoresis, sonophoresis, phonophoresis, electroporation, micro-fabricated micro-needle devices, and needle-free devices that deliver their contents by diffusion, mechanical or gas-driven energy, etc. Furthermore, devices, such as gels (thermoplastic elastomeric gels) attached to fabrics capable of delivering a topical formulation while being worn on the body are also included. These devices include oil soluble (mineral oil, etc.) mid-block copolymer gels (thermoplastic elastomer rubbery gel), which include but are not limited to: SES. (Styrene-Ethylene-Styrene), SEBS. (Styrene-Ethylene-Butylene-Styrene), SIS. (Styrene-Isoprene-Styrene), SIBS. (Styrene-Isoprene-Butylene-Styrene), SBS. (Styrene-Butylene-Styrene). In addition, oil impregnated silicone gels (alpha and beta-gels), oil impregnated silastic gels, hydrogels and proteinaceous hydrogels, hydrocolloid gels, emulsification gels (oil/protein/water and oil/water), Sol-gels, lyophilic sol gels, Elasto-gels, organo-gels, xerogels and aerogels, etc., are also included.

"Chronic administration" or "chronic application" as used herein refers to administration over a period of several days, months, years or longer. Such administration can be one or more times per day, week or month, generally from about 2 times to about 5 times, preferably 1-2 times, daily.

"Treatment" or "treating" as used herein refers to any of: the alleviation, amelioration, elimination and/or stabilization of a symptom, as well as delay in progression of a symptom of a particular condition or disorder. Accordingly, "treatment" refers to both therapeutic treatment and prophylactic or preventative measures.

The terms "individual," "subject," or "patient" are used interchangeably as used herein and refers to any vertebrate animal, more preferably a mammal, and most preferably a human, that is to be the recipient of a particular treatment. Vertebrate animals include birds or reptiles, but preferably refers to mammals such as humans, primates, canines, felines, bovines, porcines, equines, or ruminants.

The terms "acceptable topical carrier" encompasses both pharmaceutically acceptable carriers and cosmetically acceptable carriers, and which includes substantially non-irritating compatible components (either taken alone or in mixtures) which are suitable for contacting the skin.

The term "compatible", as used herein means being capable of being mixed with the seed (MFSO), skin or pulp extract(s), in a manner such that there is no interaction which would substantially reduce the efficacy of the composition during use.

A "pharmaceutically acceptable carrier" or "cosmetically acceptable carrier" includes diluents, adjuvants, and vehicles, as well as fillers, or encapsulating material that does not react with the active ingredients of the invention. Preferably, a carrier used in accordance with the subject invention is approved for animal or human use by a competent governmental agency, such as the US Food and Drug Administration (FDA) or the like. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. These formulations contain from about 0.01% to about 100%, preferably from about 0.01% to about 90% of the MFB extract, the balance (from about 0% to about 99.99%, preferably from about 10% to about 99.99% of an acceptable carrier or other excipients. A more preferred formulation contains up to about 10% MFB extract and about 90% or more of the carrier or excipient, whereas a typical and most preferred composition contains about 5% MFB extract and about 95% of the carrier or other excipients. Formulations are described in a number of sources that are well known and readily available to those skilled in the art.

An "emollient" as used herein means a suitable emollient. Examples of classes of suitable emollients include the following: (1) hydrocarbon oils and waxes such as mineral oil, petrolatum, paraffin, ceresin, ozokerite, microcrystalline wax, polyethylene, and perhydrosqualene; (2) silicone oils, such as dimethyl polysiloxanes, methylphenyl polysiloxanes, water-soluble and alcohol-soluble silicone glycol copolymers; (3) triglyceride esters, such as vegetable and animal fats and oils including castor oil, safflower oil, cottonseed oil, corn oil, olive oil, cod liver oil, almond oil, avocado oil, palm oil, sesame oil, and soybean oil; (4) acetoglyceride esters, such as acetylated monoglycerides; (5) ethoxylated glycerides, such as ethoxylated glyceryl monostearate; (6) alkyl esters of fatty acids having 10 to 20 carbon atoms such as Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate, of which methyl, isopropyl, and butyl esters of fatty acids are particularly useful; (7) alkenyl esters of fatty acids having 10 to 20 carbon atoms such as oleyl myristate, oleyl stearate, and oleyl oleate; (8) fatty acids having 10 to 20 carbon atoms such as pelargonic, lauric, myristic, palmitic, stearic, isostearic, hydroxystearic, oleic, linoleic, ricinoleic, arachidic, behenic, and erucic acids; (9) fatty alcohols having 10 to 20 carbon atoms such as lauryl, myristyl, cetyl, hexadecyl, stearyl, isostearyl, hydroxystearyl, oleyl, ricinoleyl, behenyl, erucyl alcohols, and 2-octyl dodecanol; (10) fatty alcohols ethers including ethoxylated fatty alcohols of 10 to 20 carbon atoms such as the lauryl, cetyl, stearyl, isostearyl, oelyl, and cholesterol alcohols having attached thereto from 1 to 50 ethylene oxide groups or 1 to 50 propylene oxide groups; (11) ether-esters such as fatty acid esters of ethoxylated fatty alcohols; (12) lanolin and its derivatives such as lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases; (13) polyhydric alcohols and polyether derivatives such as propylene glycol, dipropylene glycol, polypropylene glycols 2000 and 4000, polyoxyethylene polyoxyethylene glycols, polyoxypropylene polyoxyethylene glycols, glycerol, sorbitol, ethoxylated sorbitol, hydroxypropyl sorbitol, polyethylene glycols 200-6000, methoxy polyethylene glycols 350, 550, 750, 2000 and 5000, poly[ethylene oxide]homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}$-$C_{18}$ vicinal glycol, and polyoxypropylene derivatives of trimethylolpropane; (14) polyhydric alcohol esters including ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters; (15) wax esters such as beeswax, spermaceti, myristyl myristate, and stearyl stearate; (16) beeswax derivatives, such as polyoxyethylene sorbitol beeswax which are reaction products of beeswax with ethoxylated sorbitol of varying ethylene oxide content, forming a mixture of ether-esters; (17) vegetable waxes including carnauba and candelilla waxes; (18) phospholipids, such as lecithin and derivatives; (19) sterols such as cholesterol and cholesterol fatty acid esters; and (20) amides such as fatty acid amides, ethoxylated fatty acid amides, and solid fatty acid alkanolamides. Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives, comprising from about 1% to about 10% by weight of the product.

Active Agents—MFB Seed (MFSO), Skin and Pulp Extracts

MFSO

Accordingly, the invention concerns an oil or lipid extract obtained from the seeds of the *Synsepalum dulcificum* (miracle fruit). A representative composition of miracle fruit seed oil (MFSO) comprises:

1. Palmitic acid 43-46.0%;
2. Oleic acid 32-34%;
3. Linoleic acid 18-21%;
4. Stearic acid 5-7%;
5. Myristic acid 1-2%; and
6. Other fatty acids, hydrocarbons, triterpene alcohols, low molecular weight alcohols and sterols 6-8%.

One object of this invention is the use of an effective amount of MFSO extract as an active ingredient in a topical composition for treating a skin condition or a joint condition and to improve the performance of joints.

To obtain a lipid extract of the subject invention, an extraction process, and optionally one or more purification process can be carried out using hot or cold pressure extraction, extraction by solvents, or extraction by supercritical $CO_2$.

An example of an extraction process useful in accordance with the subject invention comprises contacting a finely comminuted (using a grinder) miracle fruit seed with one or more nonpolar solvent, e.g., aliphatic hydrocarbons such as hexane, vegetable oils or fatty acid esters of long-chain fatty acids such as stearic acid methyl ester.

The oil or lipid extract obtained from the seeds of the *Synsepalum dulcificum* berry (MFSO) is thick light-brown in color, having bitter taste. The oil extracted by the solvent extraction methods is obtained in 99.5% purity. The oil is water immiscible. However, it is soluble in non-polar solvents like benzene, petroleum ether, ethyl ether, acetone and hexane. The oil is also soluble in polar solvents such as ethanol and methanol.

It is found that the MFSO extracted from *Synsepalum dulcificum* is very thick and it is preferably used with a diluent. Preferably, the MFSO may be mixed with other vegetable oils. The oils that may be mixed with the MFSO include coconut oil, sesame oil, sunflower oil, olive oil, palm oil, and groundnut oil, or the like. Further, it is found that when such oils are mixed with MFSO, the penetration of the mixture into the outermost layers of the skin is enhanced to a greater extent than the MFSO used alone.

The MFSO, with or without diluent, can be added to the cosmetic or therapeutic product in raw (crude), refined, deodorized or refined and deodorized form.

This invention also includes methods of using MFSO. Although MFSO, like other vegetable oils, was expected to function as a topical lubricant, it was unexpectedly found to exhibit anti-inflammatory, antimicrobial and spermicidal activity, as demonstrated by in vitro studies conducted by or on behalf of the inventors. Therefore, any skin, hair, nail, mucous membrane or joint condition associated with inflammation or microbial activity, of which there is a multitude, may benefit from the topical use of MFSO in the form of an extract, or a composition comprising the MFSO extract, in accordance with the subject invention.

When administered topically, MFSO has been demonstrated to have a plurality of beneficial effects on conditions affecting the skin, hair, nails, mucous membranes and joints of individuals. MFSO can also improve the performance of joints when applied topically over the joints.

Studies on the oil composition of the invention suggest that topical use of MFSO is safe and effective. There are no known or demonstrated side effects of MFSO.

Skin and Pulp Extracts

Accordingly, the invention concerns a skin and pulp extract obtained from the seedless portion of the *Synsepalum dulcificum* (miracle fruit).

A representative composition of miracle fruit skin comprises: Mixtures of anthocyanin and flavonol pigments, such as cyaniding-3-monogalactoside, cyaniding-3-monoglucoside, cyanidin-3-monoarabinoside, delphinidin-3-monogalactoside, and delphinidin-3-monoaabinoside.

A representative composition of miracle fruit pulp comprises: Miraculin, the taste affecting glycoprotein of the MFB along with other free amino acids (arginine, histidine, and lysine), and unspecified anthocyanin and flavonol pigments.

One object of this invention is the use of an effective amount of MFB skin and pulp extract as an active ingredient in a topical composition for treating a skin condition.

To obtain a skin and pulp extract of the subject invention, an extraction process, and optionally one or more purification process can be carried out using hot or cold pressure extraction, extraction by solvents and alkaline for proteins, or extraction by supercritical $CO_2$.

An example of an extraction process useful in accordance with the subject invention comprises contacting the miracle fruit skin and pulp with one or more polar solvents, e.g., ethanol or methanol followed by alkaline extraction of the bound materials for harvesting the proteins.

The skin and pulp extracts obtained from the *Synsepalum dulcificum* berry are lightly tan in color, having no taste. The extracts by the solvent extraction methods is obtained in 99.8% purity. The extract is water miscible.

It is found that the MFB skin and pulp extracted from *Synsepalum dulcificum* is thick and it is preferably used with a diluent. Preferably, the extracts may be mixed with other water soluble carriers.

The skin and pulp extracts, with or without diluent, can be added to the cosmetic or therapeutic product in raw (crude), refined, deodorized or refined and deodorized form.

This invention also includes methods of using the skin and pulp extracts. It was unexpectedly found that these extracts were capable of exhibiting anti-inflammatory and antimicrobial activity, as demonstrated by in vitro studies conducted by or on behalf of the inventors. Therefore, any skin, hair, nail, or mucous membrane condition associated with inflammation or microbial activity, of which there is a multitude, may benefit from the topical use of the skin and pulp of the MFB in the form of an extract, or a composition comprising the MFB skin and pulp extracts, in accordance with the subject invention.

When administered topically, the MFB skin and pulp extracts has been demonstrated to have a plurality of beneficial effects on conditions affecting the skin, hair, nails, or mucous membranes.

Studies on the skin and pulp compositions of the invention suggest that their topical use is safe and effective. There are no known or demonstrated side effects of the MFB skin and pulp compositions.

Formulations and Carriers for Topical Administration

The MFSO, skin and pulp extracts from the MFB can be used alone in pure form for topical administration without need for a carrier. However, each of the MFB extracts can also be formulated with a carrier without negatively affecting its activity or efficacy in the treatment of a condition or its use to improve joint performance as described herein.

For ease of administration, each of the MFB extracts, according to the subject invention, may be formulated into a pharmaceutical or cosmetic dosage form, preferably a topically applied dosage form, such as a gel, cream or ointment. As appropriate compositions, there may be cited all compositions usually employed for topically administering drugs. To prepare the pharmaceutical compositions of this invention, the MFB extracts, as the active ingredients can be combined in intimate admixture with a pharmaceutically acceptable carrier, adjuvant or vehicle as desired. Such pharmaceutical compositions are desirably suitable for administration topically. The carrier can optionally comprise a penetration enhancing agent and/or a suitable wetting agent, optionally combined with suitable additives which preferably do not cause any significant deleterious effects on the skin. Said additives may facilitate the administration to the skin and/or may be helpful for preparing the desired compositions. The MFB extracts can also be combined with additives that allow the extracts to be released in controlled dosages over time, thus providing extended effects. Still further, the compositions of the present invention may be provided along with a mucoadhesive polymer excipient, for direct delivery to a mucosal surface. These compositions may be administered, e.g., as a transdermal patch, strip, film or the like or as nanoparticles, as a spot-on application, or as an ointment. Topical administration can also involve the use of vesicular concept delivery systems such as liposomes, niosomes, transferosomes, etc. In addition, other physical methods of topical delivery systems and devices may be used, such as iontophoresis, sonophoresis, phonophoresis, electroporation, and micro-fabricated micro-needle devices, etc. Furthermore, devices such as gels (thermoplastic elastomeric gels) attached to fabrics capable of delivering a topical formulation while being worn on the body may also be used. Physical modalities such as pressure, with or without occlusion, heat, cold, ultrasound, laser, radiofrequency and other forms of electromagnetic radiation can also be used to enhance the topical delivery of the composition. For topical administration the compositions can be in the form of lotions, cream, oils, ointments, serums, balms, pastes, sticks, emulsions, mousses, foams, collodions, suspensions, gels, powders, aerosols, liquids, sprays, liniments, drops suitable for administration to mucous membranes, or the like.

A lotion, cream, or ointment can be made using a liquid or semi-solid carrier. An ointment according to the subject invention may comprise a simple base of animal or vegetable oils or semi-solid hydrocarbons (oleaginous). Ointments may also comprise absorption ointment bases which absorb water to form emulsions. Examples of such ointment bases include anhydrous lanolin and hydrophilic petrolatum. Emulsion ointment bases may be oil-in-water or water-in-oil emulsions. Ointment carriers may also be water soluble. Examples of such ointment carriers include glycol ethers, propylene glycols, polyoxyl stearates and polysorbates. An ointment may also comprise from about 2% to about 10% of an emollient plus from about 0.1% to about 2% of a thickening agent. Examples of suitable thickening agents include: cellulose derivatives (e.g., methyl cellulose and hydroxypropyl methyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers.

If the carrier system is formulated as an emulsion, the composition can comprise from about 1% to about 10%, preferably from about 2% to about 5%, of an emulsifier. Emulsifiers may be nonionic, anionic or cationic.

Examples of useful nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan and hydrophilic wax esters. Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoly-2-lactylate and calcium stearoyl-2-lactylate.

Suitable anionic emulsifiers include the fatty acid soaps, e.g., sodium, potassium, and triethanolamine soaps, wherein the fatty acid moiety contains from 10 to 20 carbon atoms. Other suitable anionic emulsifies include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units.

Cationic emulsifiers useful in the present invention include quaternary ammonium, morpholinium and pyridinium compounds. Examples of such emulsifiers include dialkyl ($C_{12}$-$C_{18}$) quaternary ammonium salts, cetyl trimethyl ammonium salts; alkyl dimethyl benzyl ammonium salts, and cetyl pyridinium salts.

Single emulsion skin care preparations, such as lotions and creams, of the oil-in-water type and water-in-oil type are well known in the cosmetic art and can be employed for use with the MFB extracts of the present invention. Multiphase emulsion compositions, such as the water-in-oil-in-water type, are also useful in the present invention. In general, emulsifiers are preferred ingredients in a topical composition comprising the MFB extracts. Triple emulsion carrier systems comprising an oil-in-water-in-silicone fluid emulsion composition are also useful in the present invention.

An emulsion refers to a biphasic opaque mixture of two immiscible liquids stabilized by a surfactant. Emulsions are thermodynamically unstable systems, and usually require the application of high-torque mechanical mixing or homogenization to produce dispersed droplets. In contrast, a microemulsion is a stable biphasic mixture of two immiscible liquids stabilized by a surfactant and usually a co-surfactant. Microemulsions are thermodynamically stable and clear, form spontaneously without excessive mixing, and have dispersed droplets in an acceptable size. Both microemulsions and emulsions can be made as water-in-oil or oil-in-water systems. In a water-in-oil system, the dispersed phase is water and the continuous phase is oil. In an oil-in-water system, the dispersed phase is oil and the continuous phase is water. Whether water-in-oil or oil-in-water systems will form is largely influenced by the properties of the surfactant.

Therefore, another emulsion carrier system useful in the pharmaceutical/cosmetic compositions of the present invention is a micro-emulsion carrier system, e.g., a liposome or a NOVASOME. An example of this system comprises from about 9% to about 15% squalane; from about 25% to about 40% silicone oil; from about 8% to about 20% of a fatty alcohol; from about 15% to about 30% of polyoxyethylene sorbitan mono-fatty acid or other non-ionics; and from about 7% to about 20% water.

Lotions and creams can be formulated as emulsions as well as solutions. If the pharmaceutical/cosmetic compositions of the present invention are formulated as a gel or a cosmetic stick, a suitable amount of a thickening agent as disclosed, can be added to a cream or lotion formulation.

Creams, ointments or pastes according to the present invention are semi-solid formulations of the MFB extracts for external application. They may be made by mixing the extracts in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, *arachis*, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the MFB extracts in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

A pharmaceutical/cosmetic composition of the present invention, formulated as a liquid solution or suspension, typically includes a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the MFB extracts also possess acceptable safety (e.g. irritation and sensitization characteristics), as well as good aesthetic properties (e.g., does not feel tacky or have an unpleasant aroma). The most typical example of such a solvent is isopropanol. Other examples of suitable organic solvents include, but are not limited to: propylene glycol, polyethylene glycol (200-600), polypropylene glycol (425-2025), glycerol, 1, 2,4-butanetriol, sorbitol esters, 1,2,6-hexanetriol, ethanol, butanediol, water and mixtures thereof.

If the pharmaceutical/cosmetic compositions of the present invention can also be formulated as an aerosol and applied to the skin as a spray-on. A propellant can be added to a solution composition for aerosol use. Examples of propellants useful herein include the chlorinated, fluorinated and chloro-fluorinated lower molecular weight hydrocarbons. Other propellants useful in the present invention include lower molecular weight hydrocarbon mixtures (e.g., the mixture of butane, isobutane and propane known commercially as Propellant A46, made by Phillips Chemical Co., a subsidiary of Phillips Petroleum Company), ethers and halohydrocarbons such as dimethyl ether or dichlorodifluoromethane alone or mixtures thereof with dichlorotetrafluoroethane. Mixtures of hydrocarbon and halohydrocarbon propellants and nitrous oxide may also be used. Nitrogen and carbon dioxide can also be used as propellant gases. They are used at a level sufficient to expel the contents of the container.

The pharmaceutical/cosmetic compositions of the present invention may also be formulated as makeup products, such as foundations or lipsticks. Foundations are typically solution or lotion-based, with appropriate amounts of thickeners, pigments and fragrance. Lipsticks are composed essentially of an oil-wax base stiff enough to form a stick, with pigmentation dispersed therein.

The pharmaceutical/cosmetic compositions of the present invention may also be formulated as a gel incorporated into a thermoplastic elastomer (TPE) gel for delivery as a worn item on the skin, hair, nails, mucous membranes, and joints. Traditional thermoplastic elastomer gels are plasticized by heat and can be easily processed when molten. Styrene block copolymers are typically used in TPEGs and these polymers form a physically cross-linked network of glassy styrene domains within the mineral oil extender fluid. At temperatures below the $T_g$ of styrene, the gel is stable and does not flow, but raising the temperature above the styrene $T_g$ will cause the gel to flow. These thermoplastic properties allow for easy processing of these gels into a usable part.

For example, the MFSO can be added to oil soluble (mineral oil, etc.) mid-block copolymer gels (thermoplastic elastomer rubbery gel) that include but are not limited to: SES (Styrene-Ethylene-Styrene), SEBS (Styrene-Ethylene-Butylene-Styrene), SIS (Styrene-Isoprene-Styrene), SIBS (Styrene-Isoprene-Butylene-Styrene), and SBS (Styrene-Butylene,-Styrene). In addition, oil impregnated silicone gels (alpha and beta-gels), oil impregnated silastic gels, hydrogels and proteinaceous hydrogels, hydrocolloid gels, emulsification gels (oil/protein/water and oil/water), Sol-gels, lyophilic sol gels, Elasto-gels, organogels, xerogels and aerogels, etc., can also be used.

When attached to an article for wear on an animal or human body, these gels allow the user to deliver the MFSO to the desired areas on the body since they are capable of exuding the MFSO upon contact. Such articles can take the form of gel pads, patches, cylinders, tubes, bands, orifice/body contour shaped patches/plugs, and wearable fabric articles coated with the inventive gel compositions. The compositions described herein may be molded as independent stand-alone articles to be worn in contact with the body tissue or skin, hair, nails, and mucous membrane, or molded as composite articles with, for example, pre-formed gloves, socks, booties, cuffs, sleeves, bands, belts, pants, undergarments, or internal body cavity devices specifically designed to deliver portions of the composition to the skin, body tissue, hair or nails. In a broader sense, the body article is provided in any shape and size required to cover a particular body part. The compositions may also be molded as composite articles with polymeric and/or organic substrate films, non-woven webs, or woven fabrics that can be cut to specific sizes, shapes or shaped into articles or patches. Such articles may be constructed to form a direct delivery system for the MFSO such that when they are applied the gelatinous composition is in direct contact with body tissue, skin, hair or nails, thus providing for direct topical delivery of the MFSO included in the composition. Alternatively, articles may be constructed to form an indirect delivery system wherein a permeable membrane is interspersed between the gelatinous composition and a body tissue, skin, hair or nails.

The gel containing the composition is intimately bonded to a cloth, fabric, paper, or polymeric film substrate by blending, melting, dipping, casting, injection molding, extruding and other conventional methods. The gelatinous material is attached to cloth material on one side and the other side, when applied, directly contacts the skin, body tissue, hair or nails. The cloth material can be textile fabric constructed of either or both of a synthetic or natural fiber. Suitable synthetic materials includes fibers such as polyester, polyamide such as nylon, spandex, polyolefin, acrylic and the like fibers while suitable natural fibers include cotton, cambric, wool, cashmere, rayon, latex, jute and others.

The topical pharmaceutical/cosmetic compositions of the present invention may contain, in addition to the aforementioned components, a wide variety of additional oil-soluble materials and/or water-soluble materials conventionally used in topical compositions, at their art-established levels.

Among the optional oil-soluble materials are nonvolatile silicone fluids, such as polydimethyl siloxanes with viscosities ranging from about 10 to 100,000 centistokes at 25° C. These siloxanes are useful to enhance skin feel. These optional oil-soluble materials may comprise up to about 20% of the total composition, preferably up to about 10%.

Various water-soluble materials may also be present in the compositions of this invention. These include humectants, such as glycerol, sorbitol, propylene glycol, alkoxylated glucose and hexanetriol, ethyl cellulose, polyvinyl alcohol, carboxymethyl cellulose, vegetable gums and clays, proteins and polypeptides; preservatives such as the methyl, ethyl, propyl and butyl esters of hydroxybenzoic acid, EDTA, methylisothiazolinone and imidazolidinyl ureas; and an alkaline agent such as sodium hydroxide or potassium hydroxide to neutralize, if desired, part of the fatty acids or thickener which may be present. In addition, the topical compositions herein can contain conventional cosmetic adjuvants, such as dyes, opacifiers (e.g., titanium dioxide), pigments and fragrances.

The pharmaceutical/cosmetic compositions of the present invention may also include a safe and effective amount of a penetration enhancing (or reducing) agent. By "safe and effective amount" is meant an amount sufficient to enhance (or reduce) the penetration of the MFB extracts into the skin but not so much as to cause any side effects or skin reactions. Penetration enhancers can be provided in amounts from about 1% to about 10% of the composition.

Other known transdermal skin penetration enhancers can also be used to facilitate delivery of the composition. Illustrative are sulfoxides such as dimethylsulfoxide (DMSO) and the like; cyclic amides such as 1-dodecylazacycloheptane-2-one (AZONE, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, .α-pinene, β-carene, α-terpineol, carvol, carvone, menthone, limonene oxide, α-pinene oxide, *eucalyptus* oil, and the like. Also suitable as skin penetration enhancers are organic acids and esters such as salicyclic acid, methyl salicylate, citric acid, succinic acid, and the like.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins, that are not known to be anti-oxidants at the amounts used, may also be included in the compositions of the present invention. For example, Vitamin A and derivatives thereof, Vitamin B2, biotin, pantothenic acid, Vitamin D, or mixtures thereof, may be used in a composition in accordance with the subject invention.

For preferred topical delivery vehicles the remaining component of the composition is water, which is necessarily purified, e.g., deionized water. Such delivery vehicle compositions contain water in the range of more than about 5 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

A composition of the present invention can be stored or dispensed into a container suitable for convenient delivery, i.e., spreading, pouring, spraying, or the like. Such containers can include but are not limited to jars, bottles, lotion pumps, pump spray bottles and aerosols. The product can also be sprayed using an airbrush or any other unit that will deliver the product.

The MFB extracts can be used full strength, diluted or concentrated as desired. In general, it was determined that formulations that contain as little as from about 0.01 wt. % of the MFB extracts can be effective for treating conditions in accordance with the present invention, with formulations containing from about 0.01 wt. % to 100 wt. % being useful.

There are a wide variety of cosmetic and pharmaceutical ingredients commonly used in skin care compositions, described in a number of sources that are well known and readily available to those skilled in the art, which are suitable for use in the compositions of the present invention. Examples of these functional classes include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, waterproofing agents, and viscosity increasing agents (aqueous and nonaqueous).

Methods of Using the MFB Extracts; Seed (MFSO), Skin and Pulp

During the course of arriving at the present invention, and from studies determining the unexpected benefits of the MFB seed (MFSO), skin and pulp extracts, it was unexpectedly discovered that these extracts can be effective in treating dermatological and joint conditions. In addition, the MFSO was unexpectedly able to enhance the performance level of skeletal joints.

When administered topically, the MFB seed (MFSO), skin and pulp extracts can provide benefits for conditions affecting the skin, hair, nails, mucous membranes and joints of individuals. In addition, the MFSO applied to the joints can improve the performance of the joints of individuals. Furthermore, in in vitro studies, the MFB extracts were also unexpectedly found to exhibit, anti-inflammatory, antimicrobial and spermicidal activity.

According to various features, characteristics and embodiments of the present invention which will become apparent as the description thereof proceeds, the present invention provides a method of treating an area involving the skin, hair, nail, mucous membranes or joints from individuals suffering from dermatologic and joint conditions which involves the steps of a) providing the MFB seed, skin or pulp extract and b) applying the MFB extract to the area of skin, hair, nail, mucous membrane, or joint of individuals suffering from a condition affecting one or more of these areas of the body.

The present invention also provides a method for an improvement in the performance of skeletal motion and strength, such as for example, for improving finger dexterity and flexibility, increasing hand grip strength and steadiness, and increasing hand and finger joint mobility and endurance with a reduction in muscle fatigue, which involves the steps of a) providing the MFSO and b) applying the MFSO extract to the areas overlying the joints of individuals who desire an improvement in the performance of one or more of the joints of their body.

Provided herein are a method of use of the MFB extracts. The seed (MFSO), skin and pulp extracts may be used as an antimicrobial, anti-inflammatory, and regenerative agent for any skin, hair, nail, mucous membrane, or joint condition whose mechanism of disease formation would be impacted with any of these three activities. The uses for the skin include treating excessive dry skin using the MFB extracts as a skin moisturizer, as an anti-inflammatory for treating conditions associated with inflammation, such as atopic dermatitis and psoriasis, as a skin lubricant for medical procedures or during sexual activity, as a skin protectant for protection of skin from irritants, in wound healing and for improvements in conditions resulting in scars or scarring (e.g., keloid formation), or as an anti-aging, anti-wrinkle, skin whitening treatment, as well as treating seborrheic dermatitis with dandruff, acne (including acne vulgaris), or rosacea, or to improve or "boost" the sun-protection factor of sunscreens on the skin.

Alternatively, the MFB extracts or a composition comprising the MFB seed (MFSO), skin or pulp can be used as a cosmetic for hair or nail care, including hair softening, increasing hair shine, preventing hair breakage, or reducing split-ends. The uses for nails and mucous membranes include as a moisturizer or lubricant for brittle nails and dry lips.

Alternatively, the MFSO or a composition comprising MFSO can be used as a treatment for the reduction of joint aches or pains or to help improve the performance of the joint due to an enhanced lubrication. The goals to improve joint performance may include becoming more proficient with daily routine activities in the home or the work environment. The use of MFSO provides the joint with an ability to perform tasks faster, longer and more efficiently with greater precision. For example, an enhancement in hand and finger dexterity, flexibility, stability, steadiness, strength and endurance would be expected to lead to an improvement of the skillful performance of hand/finger activities such as typing, texting, playing an instrument, and grasping objects during everyday use, work or athletic performance. In addition, the MFSO could be used in animals to enhance the strength and stability of the ankle, thereby improving the speed of movement during daily or athletic activities. Alternatively, in addition, MFSO has spermicidal activity and can be used as a spermicidal lubricant during sex.

In the following examples of the detailed description of the preferred embodiments, reference is made to the accompanying drawings, which form a part hereof, and within which are shown by way of illustration specific embodiments by which the invention may be practiced. The examples are given solely for the purpose of illustration, and are not to be construed as limitations of the present invention. It is to be understood that other embodiments may be utilized and structural changes may be made without departing from the spirit or scope of the invention. All percentages and ratios herein are by weight, unless otherwise specified.

Source and Methods of Extraction from the Fruit Berry of the *Synsepalum dulcificum* (Miracle Fruit) Tree

Example 1

Samples And Separation Process

Source:

The Miracle Fruit crude extract samples were obtained from the berries of *Synsepalum dulcificum* (Miracle Fruit) plants grown in Miami, Florida or Ghana, Africa. At the time of their harvest, the fresh whole berries were carefully removed and refrigerated for 2-3 days prior to their processing for the extracts. The berries were removed from the refrigerator and placed in a container at room temperature for 3 hours, inspected for size and quality, and randomly selected representative lots of 100 berries were chosen for the extractions. Seeds shipped from Africa were stored in a facility prior to their processing for the oil.

Integrity and Separation of MFB Skin, Pulp (Flesh), and Seeds

Crude extracts were processed individually for each of the three separate components of the berry. Briefly, the berry samples were manually separated into skin, pulp and seeds. The berries were cut open with a razor blade, and the skin, pulp and seeds were carefully removed from each other. The pulp on the inner face of the skin was removed using an end-flattened spatula trying to carefully preserve the integrity of the skin.

Example 2

Extraction Methods

Generation of the MFB Skin and Pulp Extracts

The methods used to extract the components of the Miracle Fruit skin and pulp were modified according to procedures used by Inglett (Inglett G E. and Chen D. Contents of Phenolics and Flavonoids and Antioxidant Activities in Skin, Pulp, and Seeds of Miracle Fruit. Journal of Food Science. 2011 76(3): 479-482) and Snoussi (Snoussi, A., Hayet, BHK, Essaidi I., et al. Improvement of the Composition of Tunisian Myrtle Berries *Myrtus communis* L. Alcohol Extracts. J. Agric. Food Chem. 2012 60: 608-614). Representative examples of the extraction methods are described below:

a) The Miracle Fruit skin and pulp were separated and individually homogenized with 70% ethanol [1:10, weight (g)/volume (ml)] for one minute and then placed in the refrigerator at 4° C. for several days. The ethanol solution was either filtrated with a Whatman No. 1 paper or centrifuged at 1462×g for 15 minutes and then the supernatant-containing ethanol was removed in an evaporator set at a temperature lower than 40° C. The residue was lyophilized (freeze dried) to a solid once the ethanol was removed. The amount of residue was weighed and reconstituted with 70% ethanol at a concentration of 200 mg/ml.

Since the pulp may also contain significant quantities of carbohydrates and proteins, some which may have biological activity, these components were isolated by re-extracting the filtered residue with either 20% ethanol/water (for carbohydrates) or with alkaline extraction for bound compounds (for proteins). The solid residue from double extraction was hydrolyzed with 2N sodium hydroxide for 1 hour under nitrogen along with shaking in the dark at room temperature. The alkaline extracts were neutralized by 2N hydrochloric acid and centrifuged at 1462×g for 10 minutes. This product was freeze dried directly prior to further use.

b) The skin was finely powdered using a blender. 100 g of fine powder was soaked in 500 ml of 70% ethanol in a conical flask for 3 days at room temperature. The extract was filtered through fine muslin cloth, then filtered through Whatman No. 1 paper and evaporated to dryness using the rotary evaporator. Once the ethanol was removed, the material was freeze dried. The semi-solid extract was dissolved by using the 70% ethanol and kept at 4 C.

c) Fresh pulps were air-dried in a vacuum oven at 40° C. for 8 hours and then were pulverized to 0.2-0.4 mm powder. The material was extracted for 24 hours with 100 mL of 20% ethanol in a glass conical flask using a shaker at 25° C. and filtrated through 0.45 mm filter paper. The residue was then extracted twice with 100 mL ethanol as described above. The combined ethanol extracts were concentrated at 40° C., using a rotary evaporator under low pressure. The residue was freeze-dried and then stored in an amber colored airtight container at 4 C, prior to further use.

d) Freeze-dried solid contents: Lyophilization of frozen Miracle Fruit components gave 3.6 g (skin) and 4.2 g (pulp) of dried materials per 100 g of fresh Miracle Fruit. About 14% and 17% of the freeze-dried solids were contributed by skin and pulp respectively.

Generation of the MF Seed Oil Extracts

The MF seeds were ground into a fine powder and the oil was recovered using standard hexane and/or ethanol solvent extraction methods. The efficiency of oil extraction ranged from an 8-32% yield per extraction of the weight of the crushed seeds. Miracle fruit seeds were first ground into a fine powder mass using a grinder and subjected to analysis using small and large scale extraction methods.

Small Scale Extractions of the MFSO 5 kg extractions, 4 runs @ 4 hours per run, per extraction. Each run time was made up of a 90-minute extraction time and a 150-minute drying time. The extraction process included shaking, mixing, and decanting during each run. A 10:1 ratio of solvent to mass was used. Solvent used was a 1:1 ratio of petroleum ether to diethylether. Oil yield was between 15-18% (about 1.5-2 pounds of oil per run).

Large Scale Extractions of the MFSO 20 kg extraction was done in 1 run over 4 hours using a 10:1 ratio of solvent (hexane) to mass. 200 liters of hexane at 50° C. for 3.5 hours per run. Hexane solution was concentrated using the 100 liter rotary evaporator (rotovap) so that 70% of the hexane was recovered. Oil yield was about 19%.

Alternatively, 95% ethanol was substituted for hexane as the solvent for extractions, resulting in similar yields. When using 95% ethanol, the solution is heated to 70° C. and the solvent to mass ratio is 15:1.

Additional methods of extraction, isolation, and or preparation will be understood and within the level of skill in the relevant arts and are intended to be encompassed by the present invention.

Compositions and Formulations Containing the MFB Extracts

A variety of formulations for topical administration of the MFB extracts are contemplated for the composition of the present invention. It will be appreciated by the skilled artisan that a large number of topical formulations are known in the art, such as lotions, creams, mucoadhesive gels, vanishing lotions, vanishing creams, and the like. The making of such formulations and/or devices is well within the ability of the skilled artisan, and such formulations and methods are contemplated also by the present invention.

The MFB extracts from the different parts of the berry, either alone or in combination were used for the formulations as noted: 1) skin, 2) pulp (flesh) and 3) seed extracts were individually used or in combinations, such as 4) skin and pulp, 5) skin and seed, 6) pulp and seed, and 7) skin, pulp, and seed. The MFB extract(s) can be formulated in many types of forms for topical delivery, including but not limited to lyophilized or non-lyophilized powders, liquids, gels, creams, pastes, foams, ointments, colloidons, suspensions, emulsions, lotions, sprays, lip balms, drops, frozen fruits and dried fruits. Examples of formulations mentioned below are representative and not meant to be all inclusive.

Example 3

Hair Conditioning Composition

An example of a composition of a hair conditioning lotion containing MFSO is described. A hair conditioning lotion was prepared by combining the following components utilizing conventional mixing techniques. Composition of the hair conditioner lotion:
Theoretical Weight Percent (%)

| Ingredients | Quantity (g) |
|---|---|
| Part A- | |
| Behentrimonium methosulfate/Cetyl alcohol | 4.000 |
| Glycerin | 2.000 |
| Cyclopentasiloxane | 1.000 |
| Dimethiconol | 1.000 |
| Dimethicone | 1.000 |
| Propylparaben | 0.100 |
| Part B - | |
| Purified water | 82.100 |
| MFSO | 2.000 |
| Polyquaternium 37 | 4.000 |
| Ceteareth-20 | 1.000 |
| Methylparaben | 0.300 |
| Part C - | |
| Benzyl alcohol | 0.500 |
| Part D - | |
| Fragrance | 1.000 |

Purified water Quantity sufficient to make 100 grams total.

Add the ingredients of Part A into a suitable stainless steel kettle equipped with a propeller agitator. Mix at 77° C. to 82° C. until uniform. Add the water of Part B into a suitable stainless steel kettle equipped with a propeller agitator and begin mixing and heating to 77-82° C. Add the remaining ingredients of Part B and mix until uniform. Maintain temperature at 77 to 82° C. Add the batch of Step 1 at 77 to 82° C. to the batch of Step 2 at 77 to 82° C. and mix until smooth and uniform. Slowly cool the batch to 49 to 54° C. Add the benzyl alcohol of Part C to the batch of Step 3 at 49 to 54° C. Mix until uniform. Continue to cool the batch to 35 to 41° C.

Example 4

Composition for the Treatment of Damaged Hair

An example of a composition of a hair serum containing the MFSO and MFB pulp extract to treat damaged hair and reduce the occurrence of split-ends is described. A hair serum to treat damaged hair was prepared by combining the following components utilizing conventional mixing techniques. Composition of the hair serum:

| Ingredient | Weight % |
|---|---|
| 1. Cyclomethicone (and) Dimethiconol | 90.0 |
| 2. Trimethylsilylamodimethicone | 4.0 |
| 3. MFSO | 5.0 |
| 4. MFB Pulp Extract | 0.5 |
| 5. MFB Skin Extract | 0.5 |

Procedure: Mix ingredient 1 at medium speed with a moderate shear mixer. Slowly add ingredient 2 and continue mixing for 30 minutes after addition is complete. Slowly add ingredient 3. Continue mixing for 30 minutes after addition is complete. No heating is required.

Example 5

Skin Moisturizer Composition

An example of a composition of a skin moisturizing gel containing MFSO with anti-aging effects is described. A skin moisturizing gel was prepared by combining the following components utilizing conventional mixing techniques. Composition of the anti-aging moisturizing gel:
Theoretical Weight Percent (%)

| Ingredients | Quantity (g) |
|---|---|
| Part A- | |
| Sodium Acrylate/Acryloyldimethyl Taurate Copolymer (and) Isohexadecane (and) Polysorbate-80 | 2.000 |
| Cyclomethicone and Dimethicone Crosspolymer | 35.000 |
| Propylparaben | 0.200 |
| Part B - | |
| Purified water | 19.000 |
| Propylene Glycol | 37.000 |
| MFSO | 5.000 |
| Methylparaben | 0.300 |
| Part C - | |
| Benzyl alcohol | 0.500 |
| Part D - | |
| Fragrance | 1.000 |

Purified water Quantity sufficient to make 100 grams total.

Add the ingredients of Part A together and mix at >1,000 rpm. Mix phase B ingredients. Add Phase B to Phase A while mixing at 400 rpm. Add Phase C ingredients in order and mix at 400 rpm.

Example 6

Sunscreen Composition

An example of a composition of a cream containing MFSO and a sunscreen active agent (Octinoxate) is described below.

A sunscreen cream was prepared by combining the following components utilizing conventional mixing techniques. Composition of the sunscreen:

Theoretical Weight Percent (%)

| Ingredients | Quantity (g) |
|---|---|
| Part A- | |
| Lanolin | 4.500 |
| Cocoa butter | 2.000 |
| Glyceryl monostearate | 3.000 |
| Stearic acid | 2.000 |
| MFSO | 5.000 |
| Octinoxate | 3.000 |
| Propylparaben | 0.100 |
| Part B - | |
| Purified water | 72.600 |
| Sorbitol solution | 5.000 |
| Triethanolamine, 99% | 1.000 |
| Methylparaben | 0.300 |
| Part C - | |
| Benzyl alcohol | 0.500 |
| Part D - | |
| Fragrance | 1.000 |

Purified water Quantity sufficient to make 100 grams total.

Add the ingredients of Part A into a suitable stainless steel kettle equipped with a propeller agitator. Mix at 77 to 82° until uniform. Add the water of Part B into a suitable stainless steel kettle equipped with a propeller agitator and begin mixing and heating to 77-82° C. Add the remaining ingredients of Part B and mix until uniform. Maintain temperature at 77 to 82° C. Add the batch of Step 1 at 77 to 82° C. to the batch of Step 2 at 77 to 82° C. and mix until smooth and uniform. Slowly cool the batch to 49 to 54° C. Add the benzyl alcohol of Part C to the batch of Step 3 at 49 to 54° C. Mix until uniform. Continue to cool the batch to 35 to 41° C.

Example 7

Anti-Acne Skin Gel Composition

An example of a composition of an anti-acne skin gel containing the MFB skin extract with anti-acne effects is described. An anti-acne skin gel was prepared by combining the following components utilizing conventional mixing techniques. Composition of the anti-acne gel:

| Ingredient | Quantity (g) |
|---|---|
| Part A- | |
| Purified deionized water | 83.00 |
| Carbomer (Carbapol polymer) | 0.60 |
| Part B - | |
| Tetrasodium EDTA | 0.10 |
| Propylene Glycol | 5.00 |
| Part C - | |
| Purified deionized water | 3.00 |
| Aminomethyl propanol (AMP-95) | 0.40 |
| Part D - | |
| MFB Skin Extract | 4.00 |
| MFB Pulp Extract | 1.00 |
| Polysorbate 20 | 0.30 |
| PEG-40 Hydrogenated Castor Oil | 1.00 |
| Propylene Glycol/Methylparaben/Propylparaben/ Diazolidynil urea (Germaben) | 0.60 |
| Fragrance | 1.00 |

Procedure: Add the ingredients of Part A together by Sprinkling Carbopol on the surface of deionized water and after the polymer is thoroughly wetted, mix at >1,000 rpm. Mix phase B ingredients. Add Phase B to Phase A while mixing at 400 rpm until uniform. Mix Phase C ingredients by dissolving the AMP-95® in deionized water, add to the batch and mix at 400 rpm until uniform. Add the ingredients of PART D in order to the batch. Mix after each addition until uniform.

Example 8

Elastomer Gel Oil Exuding Wristband Containing Mf Seed Oil

Composition of Elastomer Gel

The following are exemplary gel compositions containing the MFSO. The MFSO can be contained in formulations with or without a mid-block plasticizing/solubilizing oil (mineral or a synthetic oil, etc.).

| Component | Weight % |
|---|---|
| 1) | |
| Mineral Oil (food-grade) | 78.00 |
| Kraton (blend of different MW polymers) | 17.00 |
| MFB (Seed Oil) | 5.00 |
| 2) | |
| Medium Chain Triglycerides (MCT) | 79.00 |
| Kraton (blend of different MW polymers) | 18.00 |
| MFB (Seed Oil) | 3.00 |

During the course of arriving at the present formulations, it was unexpectedly discovered that the MFSO (and other natural triglyceride oils) could be contained in a MCT oil-based elastomeric gel composition without the need for the use of a mid-block plasticizing/solubilizing oil, such as mineral oil or other synthetic oils.

The gelatinous elastomeric composition can also contain useful amounts of conventionally employed additives such as stabilizers, antioxidants, anti-blocking agents, colorants, fragrances, flame retardants, other polymers in minor amounts and the like to an extent not affecting or substantially decreasing the desired properties of the gel.

Preparation of Elastomer Gel

An exemplary gelatinous elastomer composition formulation containing the MF seed oil was prepared as described by Gould (U.S. Pat. No. 6,673,054) with modifications as follows. Oil portions, containing the pre-blended mineral oil and MF seed oil were heated to between 150° C.-175° C. Liquid portions of formulations were added to copolymers in a heated vessel properly equipped to blend the materials homogeneously with minimal entrainment of air. All ingredients were combined and mixed in the heated vessel with a stirrer to homogeneity.

Attachment of the Elastomer Gel to the Fabric of the Wristband

A representative example is the attachment of the elastomer gel to the wristband fabric. The above gel composition comprising the active formulation containing the MF seed oil additive was intimately bonded to the fabric by conventional methods. For example, a preselected rigidity of the molten gelatinous elastomer composition was cast directly onto the cloth fabric material to form the wristband. The gelatinous elastomer composition could also have been die cast, cut to size and heat bonded to the fabric. Likewise, the fabric can be dipped into a preselected rigidity of a molten gelatinous elastomer composition and re-dipped into the same or different composition of a different rigidity. The shaped gel can be conventionally covered with fabric as needed.

Exudation of the Oil from the Gel Formulation to a Surface

Exudation of oil from the gelatinous composition was determined as previously described by Matteliano (U.S. Pub. No. 2010/0063008 A1). Briefly, sample filter paper discs were placed in contact with the gel of the same diameter under constant low pressure at 37° C. Multiple timed exposures of the filter paper to the gel were performed in succession to the gel in duplicate. The average rate of the exudation of the oil from the elastomer gel was 2.60 mg/cm$^2$/hour at 37° C. (after 1 hour elapsed of continuous exudation).

This exemplary TPE gel may be prepared using the preparative methods of the present invention as outlined above, and other methods that are well known in the art for making TPE gel compositions.

Example 9

Anti-Inflammatory Activity

MFSO and the MFB skin extract have Anti-inflammatory Activity. In vitro experiments were performed to demonstrate if MFSO and MFB skin extract have anti-inflammatory activity by inhibiting the induction and release of the inflammatory mediator LTB4 from macrophages.

MFSO and the MFB skin extract were dissolved in DMSO and added to cell culture medium at a stock concentration for use in these in vitro experiments. The ability of MFSO to function as an inhibitor of LTB4 release was evaluated using a macrophage cell line followed by the addition of calcium iontophore for stimulation of LTB4 and the use of a radioimmunoassay (Amersham) for LTB4 detection as previously described (Garrido G, González D, Lemus Y, Garcia D, Lodeiro L, Quintero G, Delporte C, Núñez-Sellés A J, Delgado R. In vivo and in vitro anti-inflammatory activity of *Mangifera indica* L. extract (VI-MANG). Pharmacol Res. 2004 August; 50 (2):143-9). NDGA (25 uM) is a known positive control that inhibits LTB4 release and the vehicle control consisted of DMSO in culture medium with no MFSO.

MFSO (n=3) and the MFB skin extract (n=2) were effective and showed considerable activity in suppressing LTB4 release from macrophages that were stimulated with calcium iontophore. An MFSO and a MFB skin extract (concentration of 10$^{-3}$%) were capable of inhibiting LTB4 release by 53% and 36%, respectively. NDGA, used as a known LTB4 inhibitor, produced an inhibition of 98%.

MFSO has anti-inflammatory activity directed against LTB4 release at concentrations not affecting cell cytotoxicity in vitro.

Example 10

Antibacterial And Antifungal Activity

MFSO has Antimicrobial Activity against Common Bacterial and Fungal pathogens (Table 1). In vitro experiments were performed to demonstrate MFSO has broad spectrum antimicrobial activity against common bacterial and fungal pathogens.

MFSO was dissolved in DMSO in culture medium for use in these in vitro experiments. The ability of MFSO to function as an antimicrobial was evaluated using the Agar-solid Diffusion Method as described (Leite S P, Vieira J R, de Medeiros P L, Leite R M, de Menezes Lima V L, Xavier H S, de Oliveira Lima E. Antimicrobial Activity of *Indigofera suffruticosa*. Evid Based Complement Alternat Med. 2006 June; 3 (2):261-5). The inhibition zones produced by MFSO were compared with the inhibition zones produced by commercial standard antibiotics that served as positive controls. The DMSO solvent in culture medium was used as the negative control. The organisms were designated arbitrarily as sensitive or resistant. The zones were measured at the end of the incubation time. An inhibition zone of 10 mm or greater was considered indicative of good antimicrobial activity.

Table 1 summarizes the inhibitory growth of the organisms tested with MFSO.

TABLE 1

Values of Inhibition Zone (mm) by MIC Determination of MFSO against Bacterial and Fungal Activities

| Organism | MFSO (% Concentration) | | | | *Organism Growth Without Anti-microbials | Chloramphenicol (30 uM) | Ketoconazole (1 mM) | Ciprofloxacin (10 uM) |
| --- | --- | --- | --- | --- | --- | --- | --- | --- |
| | 1 | 5 | 10 | 20 | | | | |
| Staph Aureus | 0 | 6 | 9 | 12 | + | 25 | 0 | 25 |
| P. Acnes | 7 | 12 | 22 | 23 | + | 25 | 0 | 22 |
| E. Coli | 0 | 7 | 9 | 10 | + | 0 | 0 | 25 |
| C. Albicans | 0 | 6 | 8 | 10 | + | 0 | 25 | 0 |
| T. Rubrum | 0 | 8 | 12 | 16 | + | 0 | 25 | 0 |

*+ = growth

MFSO was effective and showed significant antimicrobial activity directed against common bacterial and fungal organisms. MFSO provided its strongest antimicrobial activity against *P. Acnes* and *T. Rubrum*, zones of inhibition>10 at 10% MFSO. These inhibitory activities by MFSO were significantly different (p<0.05) from those seen against *S. Aureus, E. Coli,* and *C. Albicans*, which showed minimal inhibitory activity seen only at the highest concentration of MFSO tested (20%).

MFSO has antimicrobial activity against common bacterial and fungal organisms in vitro. The antimicrobial activity is greatest against *P. Acnes* and *T. Rubrum* indicating that patients with acne and ringworm infections could derive benefit from its use.

In similar studies, a MFB skin extract was effective and showed significant antimicrobial activity directed against *P. Acnes* organisms in vitro, with zones of inhibition>10 at concentrations of 10% or higher of the MFB skin extract (data not shown).

Example 11

Antiviral Activity

MFSO has Antimicrobial Activity against Common Viral Pathogens (Table 2). In vitro experiments were performed to demonstrate MFSO has antiviral activity and can inactivate commonly encountered infectious enveloped viruses.

MFSO was dissolved in DMSO in culture medium for use in these in vitro experiments. Herpes simplex virus type 1 (HSV-1) and Influenza-A (INF) virus strains were obtained from the ATCC and grown in Vero cells. Viruses were titrated by inoculations of serial 10-fold dilutions into Vero cells contained in 96-well microtiter tissue culture plates and virus titers calculated by the Reed and Muench method (Shao L, Sun X, Fang Q. Antibodies against outer-capsid proteins of grass carp reovirus expressed in *E. coli* are capable of neutralizing viral infectivity. Virol J. 2011 Jul. 12; 8:347). The calculated titers of the virus stocks used for these experiments were 4.5 TCID50.

The ability of MFSO to function as an inactivating agent for enveloped viruses was evaluated using the TCID50 inactivation assay (Thormar H, Isaacs C E, Brown H R, Barshatzky M R, Pessolano T. Inactivation of enveloped viruses and killing of cells by fatty acids and monoglycerides. Antimicrob Agents Chemother. 1987 January; 31 (1): 27-31). The $10^{-2}$ to $10^{-4}$ dilutions were inoculated into monolayers of Vero cells. Virus alone in culture medium with DMSO was the positive control and the culture medium with DMSO served as the negative control. The difference between the titer ($\log_{10}$) of the control virus and the titers of the virus+MFSO mixtures (after a 1-minute exposure prior to inoculation into the cell cultures) was considered the reduction of virus titer, which is the measure of viral inactivation.

Table 2 summarizes the level of viral inactivation after both enveloped viruses were exposed to different concentrations of MFSO.

TABLE 2

Inactivation of Enveloped Viruses by MFSO

| MFSO (% Concentration) | Reduction of Virus Titer ($\log_{10}$ TCID50) | |
|---|---|---|
| | HSV-1 | Influenza-A |
| 1 | 0 | 0 |
| 5 | 1.0 | 1.0 |
| 10 | ≥3 | ≥3 |
| 20 | ≥3 | ≥3 |

MFSO concentrations of 10% or greater were capable of inactivating ≥3 $\log_{10}$ TCID50 virus titers. The difference in the inactivation of viral titers was significant (p<0.05) for concentrations of 10% MFSO or greater when compared to MFSO concentrations of 5% or less (0-1 $\log_{10}$ TCID50 reductions in viral titers).

MFSO can inactivate enveloped viruses and lead to significant reductions of virus titers of HSV-1 and INF-A viruses in vitro. The reductions in virus titers are greatest at MFSO concentrations of 10% or greater.

Example 12

Spermicidal Activity

MFSO has Spermicidal Activity (Table 3). In vitro experiments were performed to demonstrate MFSO has the capacity to act as a spermicidal agent.

Normal human spermatozoa were used to assess the spermicidal activity (Sander-Cramer assay) of MFSO as described (Benhong Z., Zhenpeng Q, Gang L, Chun L, Zhang J. Spermicidal and antigonococcal effects of tannins from pomegranate rind. Journal of Medicinal Plants Research 2012 February; 6 (7); 1334-1339). Nonoxynol-9 was used as a positive reference standard and semen added to physiological saline was used as the negative control. Semen samples were donated by 3 healthy fertile men. The minimum MFSO concentration that caused 100% immobilization of sperm within 20 seconds was considered to be the minimal effective concentration (MEC).

Table 3 summarizes the spermicidal activity of sperm treated with MFSO.

TABLE 3

Inactivation of Sperm by MFSO

| MFSO (% Concentration) | *Sperm Motility (Action Time in Seconds) | |
|---|---|---|
| | 20 | 60 |
| 1 | + | + |
| 5 | ± | ± |
| 10 | − | − |
| 20 | − | − |
| Nonoxynol-9 (1%) | − | − |
| Physiological Saline | + | + |

*+ = Mobile, − = Immobile, ± = 90% lost mobility

MFSO immobilized and killed 100% of the spermatozoa within 20 seconds in vitro at the concentrations of 10% (the MEC) or greater. Of note, at a 5% MFSO concentration, spermatozoa were immobilized within 40 seconds.

MFSO has spermicidal activity in vitro. At 10% MFSO or greater, 100% of sperm become immobile within 20 seconds of exposure.

Example 13

Improvement for Hair

A) Hair Samples
Hair Preparation

The tresses of virgin dark-brown and bleached hairs were obtained from De Meo Brothers Inc. (NY, USA). The hair samples were about 8 inches in length and approximately 3 grams in weight. The tresses were washed and cleaned twice with a solution of lauryl sodium sulfate solution (4.5% w/w) in deionized water. The tresses were rinsed under warm running water (38° C.) for 30 seconds between washings and for 60 seconds after the second washing. Excess water was squeezed from the tresses by pulling them between two fingers. The tresses were combed using a polypropylene comb to carefully detangle the hairs and stored at ambient temperature (22°-24° C. @ 50-55% relative humidity) prior to use.

Hair treatment: 0.5 ml of oil (with or without absolute ethanol as the reference base solvent) was applied to each tress and massaged or rubbed on it for 1 minute. The tresses were rinsed for 30 seconds with warm running water (38° C.) at a flow rate of 1 gallon/minute. For wet combing, the tresses were then kept in a climate controlled area at ambient conditions for 30 minutes before the measurements. For repeated brushing studies, the tresses were kept in a climate controlled area at ambient conditions and allowed to fully air-dry and equilibrate under controlled humidity conditions prior to the measurements.

B) Hair Treatment

1. MFSO Reduces the Wet Combing Force on Hair Tresses.

A study was performed to demonstrate the application of MFSO to wet hair tresses can lead to a reduction in the wet combing force.

The measurements of wet combing force were performed using a 4301 Instron Machine with the comb fixed accessory developed by an engineer, using a speed of 500 mm/min and a 10N load cell (Fregonesi A, Scanavez C, Santos L, De Oliveira A, Roesler R, Escudeiro C, Moncayo P, De Sanctis D, Gesztesi J L. Brazilian_oils and butters: the effect of different fatty acid chain composition on human hair physiochemical properties. J Cosmet Sci. 2009 March-April; 60 (2):273-80). Tresses of bleached dark-brown hair 20 cm long and weighing 3 g were used. Before the measurements the tresses were manually combed once for disentanglement. The results of the wet combing experiments (reported in percentage reduction of combing force) were expressed as the average of 8 tresses per each treatment (one time per tress). The measurements of force were recorded after the $6^{th}$ groom stroke (the $1^{st}$ 3 groomed strokes were used to remove any remaining tangles) which showed that the combing force for each stroke prior and after the $6^{th}$ stroke were approximately the same (nearly identical superimposed force curve) as the combing force of the $6^{th}$ stroke. The measurements of reference conditions (using absolute alcohol alone) were realized before the application of oils to the tresses. The wet combing was performed to the tresses after 30 min of the treatment at 25±5° C. For this test, the tresses were maintained in a small climate controlled room at 50±10% RH and 25±5° C. Statistical analysis was performed using the t-test at 95% confidence level.

FIG. 1 shows the average values of the wet tress reduction of combing force (%) after treatment with different concentrations of MFSO. The MFSO-treated hair tresses exhibited a concentration-dependent reduction in wet combing force. Oil treatment with pure MFSO rendered about a 70-80% reduction of combing force at wet conditions compared to the controls, the untreated reference or the ethanol base. Absolute ethanol (base), however, increased the combing force giving negative values for the reduction of combing force percentage. Ethanol is known to be very drying to the hairs and does not spread easily along hair tresses, thereby making the hairs much stiffer to comb. Mineral oil (control) also reduced the wet combing force. However, the level of wet comb force reduction with mineral oil was lower than that seen with the MFSO.

The use of MFSO in wet hair produced a statistically significant % reduction in the combing force when compared to the reference (untreated) or the ethanol base. The reduction of combing forces is most likely due to the combination of water wetting and the lubricant effects of the oil on the hair fibers.

2. MFSO Reduces Hair Breakage During Repeated Brushing Experiments on Hair Tresses.

A study was performed to demonstrate the application of MFSO can reduce the level of hair breakage during repeated brushing studies of hair fibers.

The hair tresses were submitted to cycles of combing using combing equipment that was developed by an engineer that simulates the daily care combing. The equipment was automatically operated and had an accessory with four fixed combs that moved in a circle with a speed 50 strokes/min, permitting a combing of the tresses (20 cm and 3 g) that were fixed in position in front of the equipment. The tresses were groomed in a block of 1,000-strokes at ambient conditions and 60% relative humidity with subsequent counting of the broken fibers in the collection tray under the tress (Evans T A, Park K. A statistical analysis of hair breakage. II. Repeated grooming experiments. J Cosmet Sci. 2010 November-December; 61(6):439-55. Erratum in: J Cosmet Sci. 2011 May-June; 62 (3):359).

Figure 2:
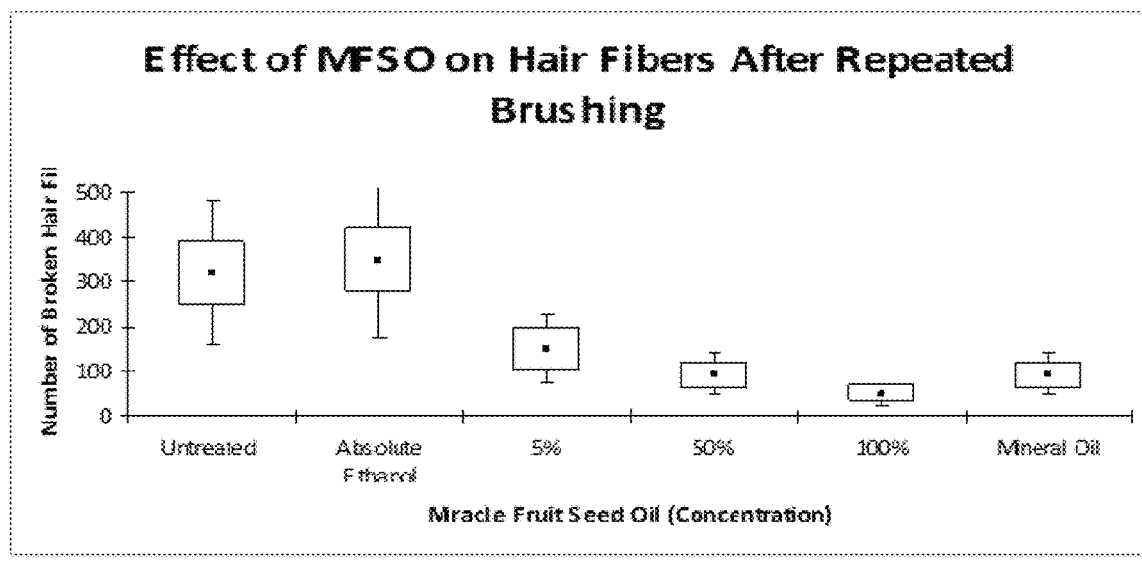
FIG. 2 is a graph depicting that MFSO reduces hair breakage during repeated brushing experiments on Hair Tresses in vitro.

FIG. 2 shows the mean values of the number of broken hair fibers after 1,000 brushes grouped by treatment. Treatments using MFSO-treated hair tresses reduced the numbers of broken hair fibers compared to the reference (untreated control) and the base (absolute ethanol). The MFSO-treated hair tresses exhibited a concentration-dependent decrease in broken hair fibers. Tresses treated with pure MFSO had the lowest numbers of broken hair fibers, which led to approximately an 85% reduction compared to the untreated or base ethanol controls.

MFSO significantly reduced the number of broken hair fibers after 1,000 brushes when compared to the untreated and base controls. MFSO performed better than mineral oil in its ability to reduce hair breakage.

3. MFSO Reduces the Formation of Split Ends in Hair Fibers.

A study was performed to demonstrate the use of MFSO can reduce the formation of split ends in hair fibers.

Using the repeated brushing equipment, cycles of combing and drying (1 hour) were implemented using a hair dryer (1800 W) that was put 5 cm distant from the tresses at 70° C. (Fregonesi A, Scanavez C, Santos L, De Oliveira A, Roesler R, Escudeiro C, Moncayo P, De Sanctis D, Gesztesi J L. Brazilian_oils and butters: the effect of different fatty acid chain composition on human hair physiochemical properties. J Cosmet Sci. 2009 March-April; 60 (2):273-80). After the time, the formation of split ends was quantified by visual counting (number of split ends per gram of hair).

Figure 3:
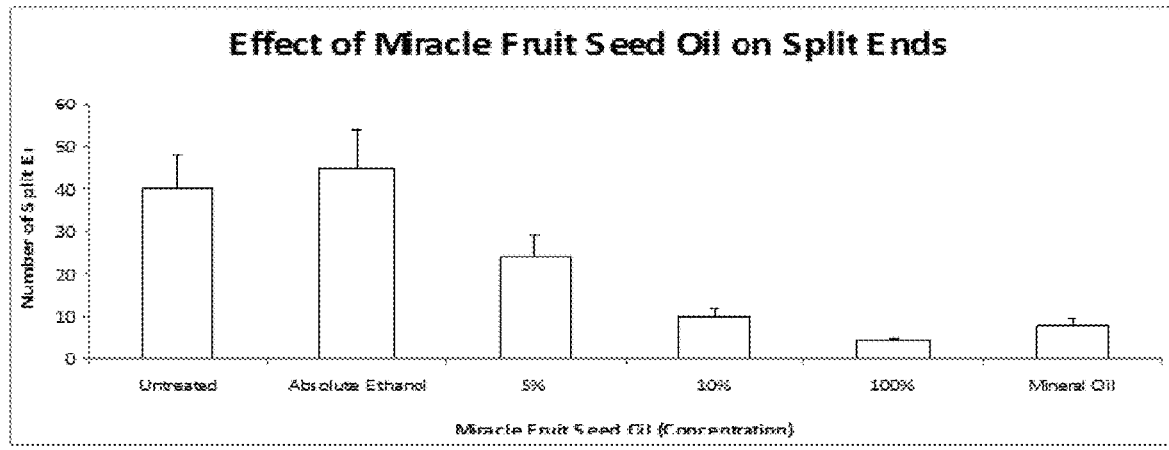
FIG. 3 is a graph depicting that MFSO reduces the formation of split ends in hair fibers in vitro.

FIG. 3 shows the average values of the number of split ends per gram of hair formed during the extensive process of combing during hot drying for one hour after the application of the MFSO treatment. Treatments using MFSO reduced the formation of split ends in the hair fibers compared to the reference (untreated control) and the base (absolute ethanol). There was a concentration dependent decrease in the numbers of split ends with increasing MFSO concentration. Tresses treated with pure MFSO gave the lowest formation of split ends, which was around 4-9 split ends per gram of hair. MFSO was effective and also superior to pure mineral oil in its effect on reducing the formation split ends in hair fibers.

Similar studies using a hair serum containing an MFB pulp and skin extract formulated with silicones revealed a substantial reduction in split ends when compared to controls (data not shown).

4. MFSO Reduces Hair Breakage in a Clinical Study of Long-Haired Women.

A clinical study was performed to demonstrate that MFSO has the ability to reduce hair breakage in long-haired women.

Chemical hair care treatments have routinely been evaluated for their anti-hair breakage performance in the laboratory setting using sophisticated mechanical instrumentation as described previously in this application. However, the invention of the cross-sectional trichometer, a newly developed quantitative hair breakage measuring device, provides a novel method that is applicable to measure hair breakage in clinical studies (Cohen B. The cross-section trichometer: a new device for measuring hair quantity, hair loss, and hair growth. Dermatol Surg. 2008 July; 34 (7):900-10) and (Mhaskar S, Kalghatgi B, Chavan M, Rout S, Gode V. Hair breakage index: an alternative tool for damage assessment of human hair. J Cosmet Sci. 2011 March-April; 62 (2):203-7).

The purpose of the clinical study was to determine if a hair care conditioning product containing MFSO compositions was effective in the prevention of hair breakage, as measured using a cross-sectional trichometer, in long-haired female subjects that routinely use physically damaging modalities on their hair. Under the supervision of a physician at a third-party medical facility (no conflict of interest), a 4-month clinical study was performed.

Hair breakage was measured using the cross-sectional trichometer.

The hair breakage index (HBI) was measured as follows:

HBI=(proximal cross-sectional area−distal cross-sectional area)×100/proximal cross-sectional area After 3 months of use, patients treated with hair conditioners containing the MFSO oil compositions had significantly less hair breakage (P<0.05), a 40% reduction in HBI measurements when compared to subjects that continued using their leading commercial hair care conditioner brands, as measured with a cross-sectional trichometer.

Example 14

Use as Skin Moisturizer, Lubricant & Barrier

A. MFSO is an Effective Skin Moisturizer for Dry Skin.

A clinical study was performed to demonstrate an MFSO lotion can effectively moisturize the skin and maintain its barrier function for a prolonged period of time.

10 patients (ages 35-75 years) with moderate to severe dry skin, two of which had atopy, involving the lateral aspect of the lower leg were selected. Sites were marked with a template and 2 mg of test lotions, one containing 5% MFSO and the other 5% mineral oil, were applied per square centimeter to each treatment site (multiple replicates) one time only. Untreated sites served as controls. The Corneometer® (Courage & Khazaka) and the DermaLab® (Cortex Technology) devices, which measure the relative hydration of the stratum corneum and the skin barrier function as trans-epidermal water loss (TEWL), respectively, were used to evaluate the hydration and barrier function of the skin. These bioinstrumentation measurements were taken and recorded at baseline and at different time intervals over a 48 hour period after the one-time application to treatment sites on the lower leg.

FIG. 4 shows the results of a) The Corneometer® and the b) DermaLab TEWL® devices used to evaluate the hydrating effects of a MFSO lotion in a kinetic dry skin study of the lower leg. The data in the figure are expressed as the mean±SD.

Figure 4A:
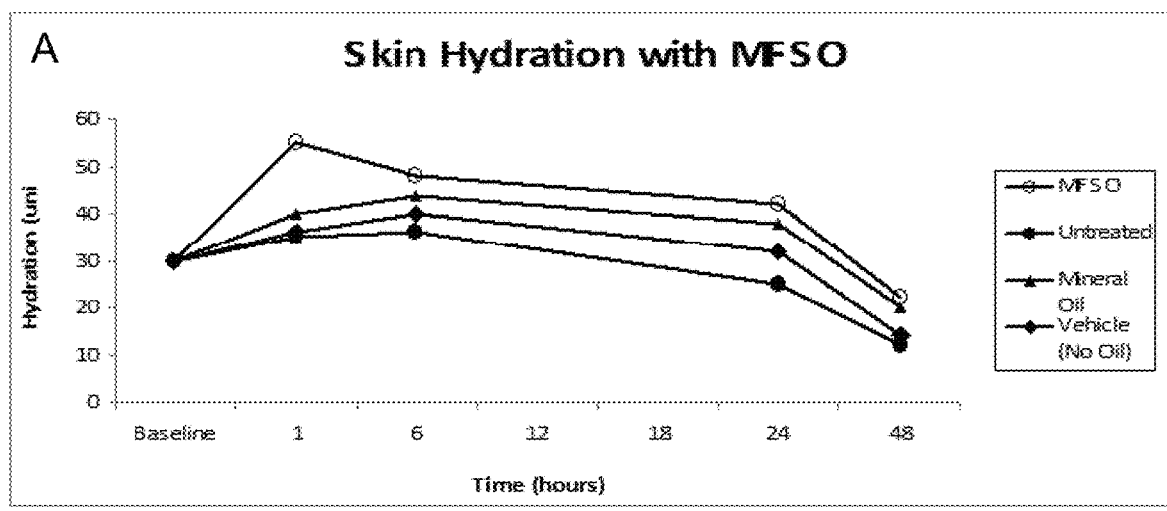
FIG. 4 (A-B) illustrate graphs depicting that MFSO functions as a skin moisturizer in vivo.

The skin hydration studies showed that both lotions demonstrated significant improvements (p<0.05) in skin surface hydration compared to baseline (FIG. 4a). Sites treated with the MFSO lotion had significantly higher conductance values (p<0.05) when compared to sites treated with the mineral oil lotion during the initial 24 hours. This study demonstrated that after one application of the MFSO lotion, it effectively moisturized the stratum corneum of the skin for up to 24 hours when compared to the baseline values and the untreated control.

Figure 4B:
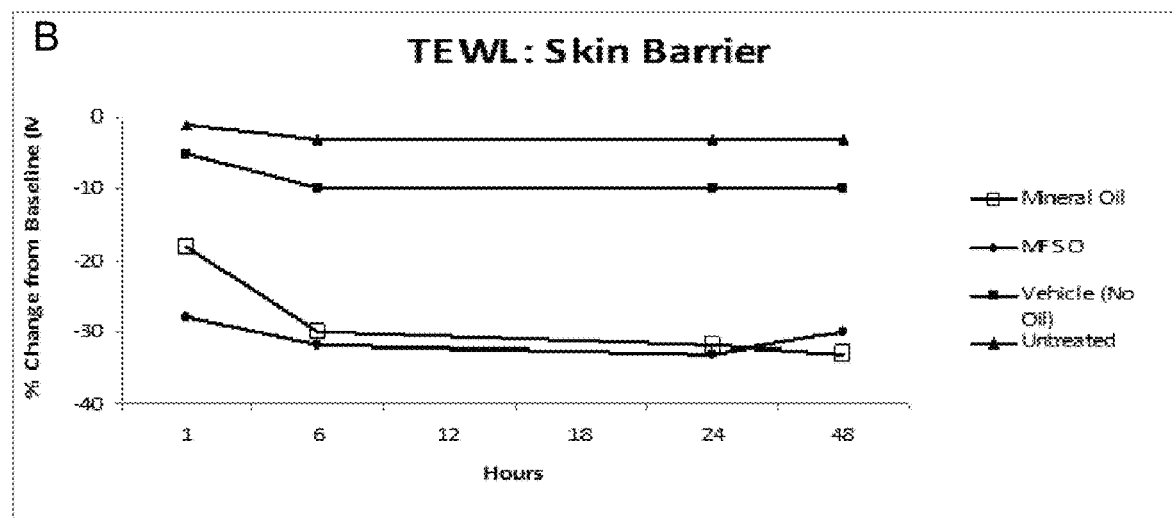

The TEWL results indicated that the MFSO lotion caused a rapid and significant improvement in skin barrier function (1 hour) which was not seen with the mineral oil lotion (FIG. 4b). Only the MFSO lotion showed a significant improvement in TEWL values from baseline. Both products showed an average of greater than 30% improvement in TEWL values after 6 hours and beyond (the differences in TEWL measurements between the test lotions were not significant). This clinical study demonstrated that the MFSO lotion enhanced barrier repair more rapidly than the mineral oil lotion. In two patients that were studied, the MFB skin and pulp extracts were also capable of improving the skin surface hydration (data not shown).

B. MFSO is an Effective Skin Lubricant for Sexual Activity.

A clinical study was performed to demonstrate MFSO formulated in a silicone-based serum is an effective skin lubricant for sexual use when applied to skin and mucous membranes of the genitals.

5 subjects (3 males and 2 females) were enrolled in an open label blinded study. They were instructed to either apply a MFSO containing lubricating serum or the base (lubricant serum with no MFSO) a few minutes before engaging in their routine sexual activity. After 1 month of use, they were asked to compare the efficacy of both products.

All 5 patients subjectively agreed that they preferred and performed better with the MFSO lubricant when compared to the lubricant base with no MFSO. This pilot clinical study demonstrated that MFSO in a silicone base is an effective lubricant for use during sexual activity.

C. MFSO is Effective in Protecting the Skin from Irritation.

Chemical irritants can damage the stratum corneum and thus compromise its barrier function. A clinical study was performed to demonstrate an MFSO containing lotion can effectively protect the skin and act as a barrier from a chemical irritant exposure.

6 subjects (ages 35-55 years) were selected. Initial preliminary studies revealed that 2% SLS (3 repeated exposures to the forearm) produces a chemical irritation leading to increases in TEWL and the visible clinical signs of erythema and edema (Farage M A, Ebrahimpour A, Steimle B, Englehart J, Smith D. Evaluation of lotion formulations on irritation using the modified forearm-controlled application test method. Skin Res Technol. 2007 August; 13 (3):268-79). Forearm sites were marked with a template and repeated exposures of 2 mg per square centimeter of 2% sodium lauryl sulfate (SLS) chemical irritant was applied to test sites. Five minutes prior to the third and final exposure of SLS, 5% MFSO or 5% mineral oil lotions were applied to the treatment sites (one time only with multiple replicates). 30 minutes after the application of the SLS, the sites were measured for TEWL using the DermaLab TEWL device. Untreated blank sites served as controls. The investigator assessed objective irritation parameters (erythema and edema) using a 4-point scale where 0=none, 1=mild, 2=moderate, and 3=severe (half points scores were allowed).

Figure 5A:
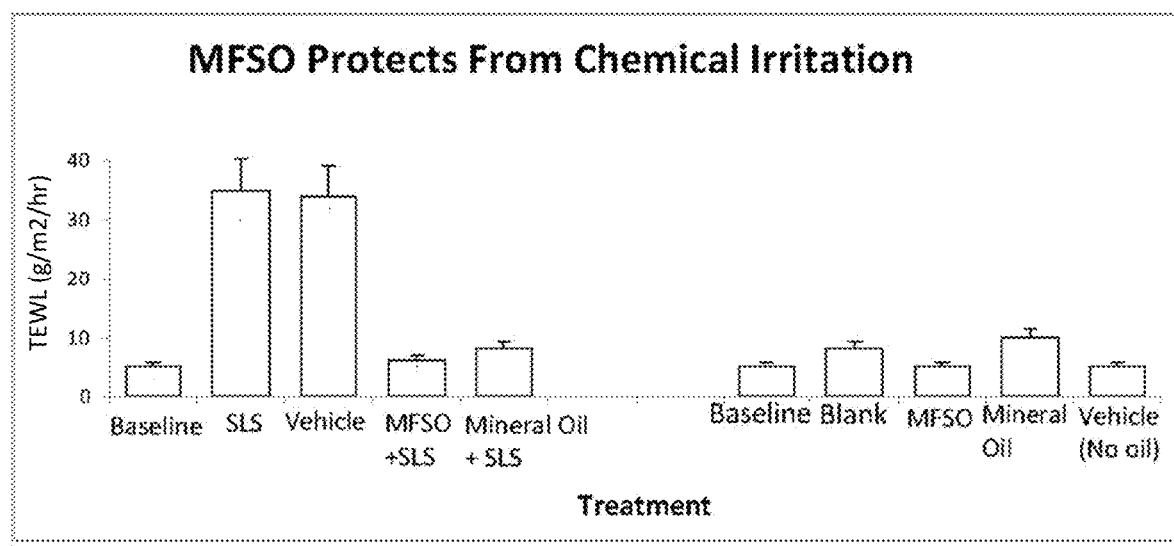
FIG. 5 (A-B) illustrate graphs depicting that MFSO functions as a barrier and protects the skin from chemical irritation in vivo.
Figure 5B:
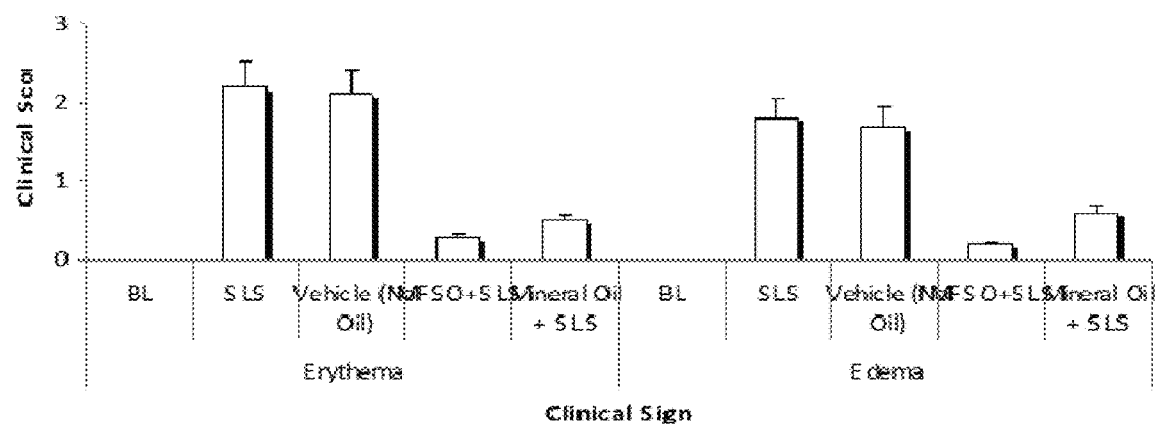
Figure 6A:
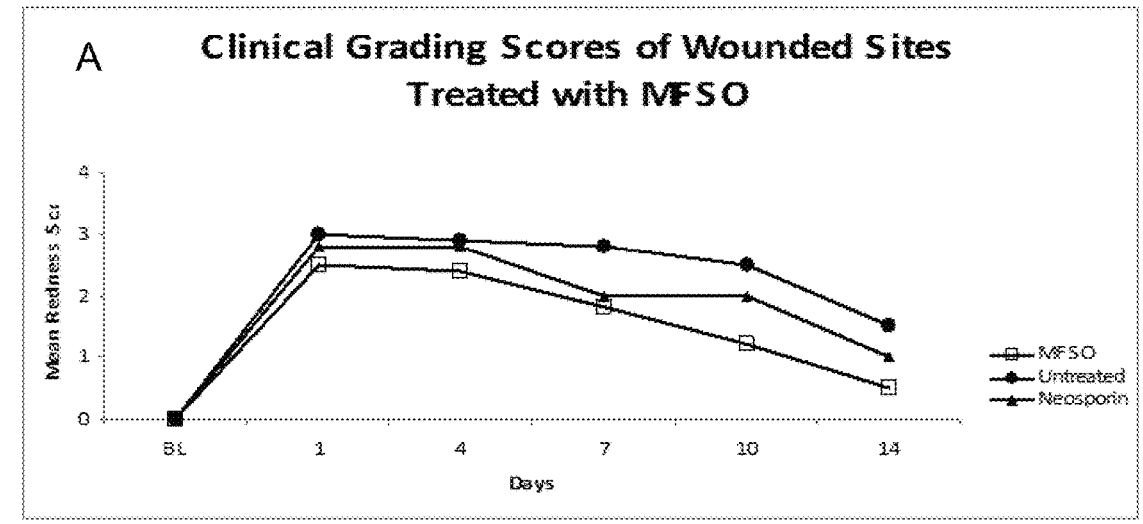
FIG. 6 (A-D) illustrate graphs depicting that MFSO improves wound healing in vivo.
Figure 6B:
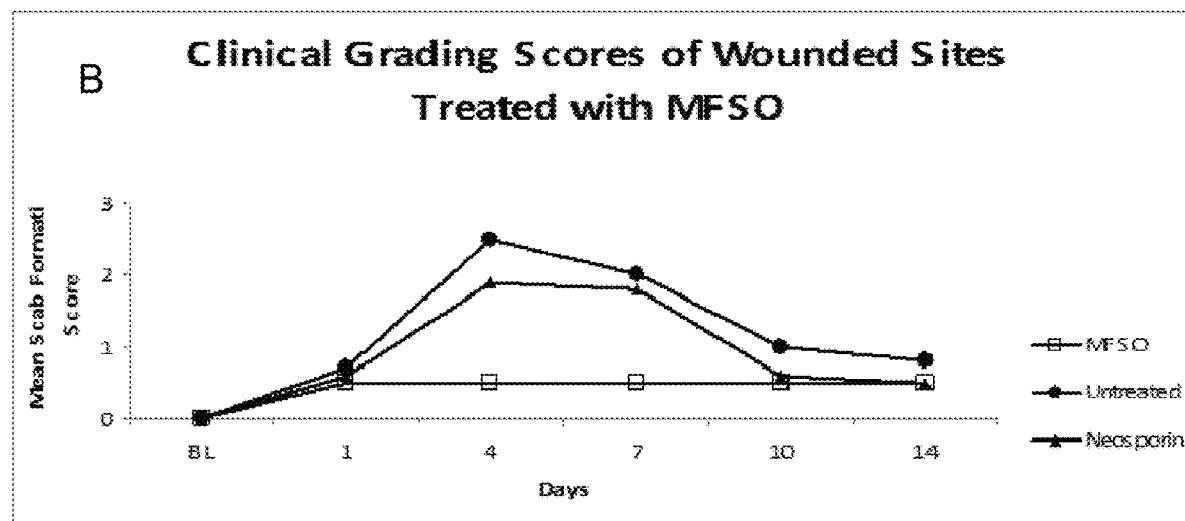
Figure 6C:
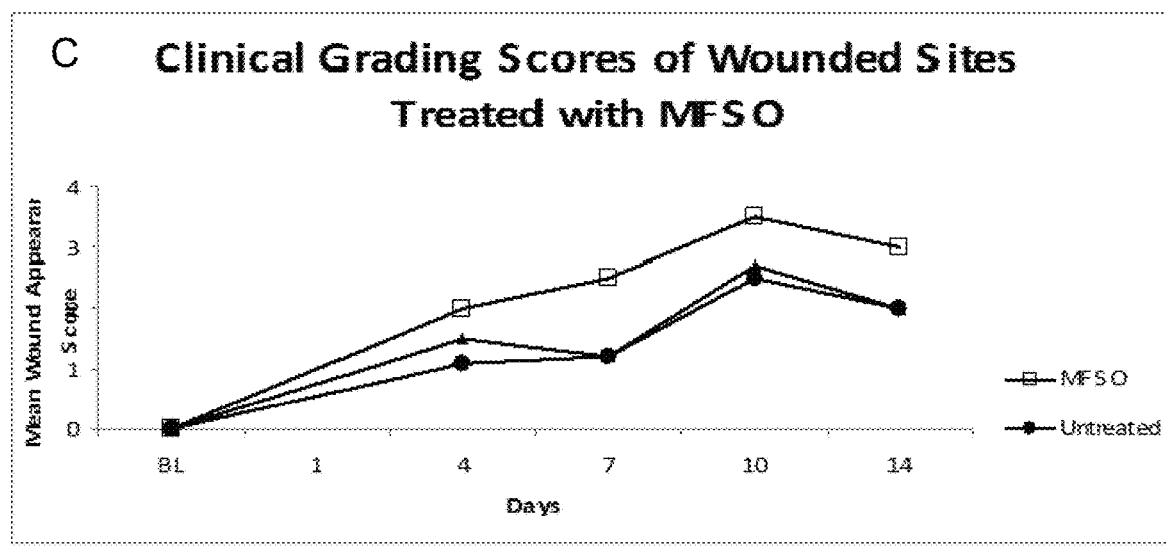
Figure 6D:
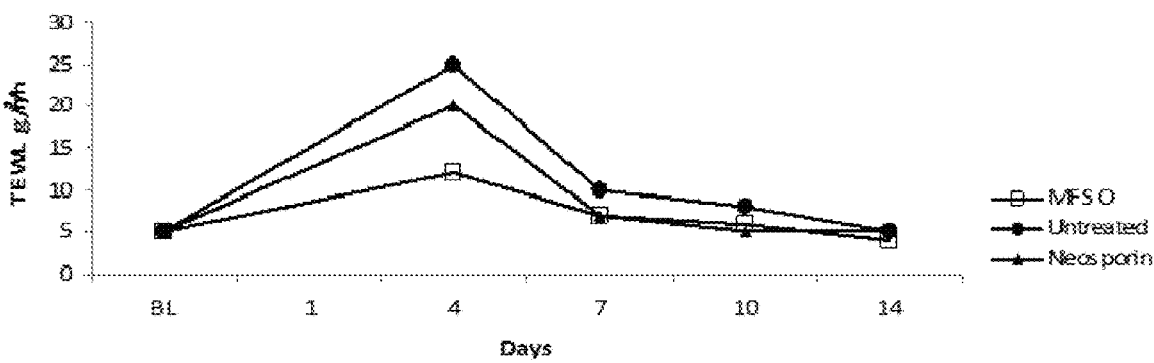

FIG. 5 shows the ability of the MFSO lotion to act as a barrier and protect the skin from a chemical irritant (2% SLS) exposure as shown by a) TEWL measurements and b) the clinical signs of erythema and edema. The data in the figure are expressed as the mean±SD. The MFSO lotion used prior to the SLS application on the skin showed a significant reduction ($p<0.05$) in the level of TEWL when compared to the skin sites exposed to 2% SLS. Analysis of the data also showed significant differences ($p<0.05$) in the reduction of the severity scores for the clinical signs of erythema and edema with the use of the MFSO lotion when compared to the sites treated with 2% SLS.

The skin irritation studies demonstrated that the MFSO lotion can act as a skin protective agent when applied to the skin sites prior to the application of the skin irritant. The increases in TEWL and the visible clinical signs of erythema and edema produced with the use of the skin irritant were significantly prevented with the prior use of the MFSO lotion.

Example 15

Treatment of Wounds

A. MFSO Improves Wound Healing.

A pilot clinical study was performed to compare the wound healing properties of a MFSO containing ointment to Neosporin® ointment (Poly/Bac/Neo; Johnson & Johnson, New Brunswick, NJ) using a laser wound model.

3 uniform and circular laser wounds penetrating to the superficial dermis were made using an erbium/carbon dioxide laser in 3 subjects (Trookman N S, Rizer R L, Weber T. Treatment of minor wounds from dermatologic procedures: a comparison of three topical wound care ointments using a laser wound model. J Am Acad Dermatol. 2011 March; 64 (3 Suppl):S8-15). Each wound was treated once daily for 14 days using an MFSO containing ointment or Neosporin® ointment (one wound served as an untreated control). Efficacy was assessed using mean clinical grading scales for redness and scab formation, investigator grading of clinical mean would appearance, and TEWL (biomechanical measurements with the DermaLab TEWL device). Redness grading scale: 0=none, 1=mild, 2=moderate, 3=marked, 4=severe. Scab formation grading scale: 0=none, 1=slight, 2=moderate, 3=extensive, 4=complete or nearly complete. Wound appearance grading scale: 0=poor, 1=fair, 2=good, 3=very good, 4=excellent.

FIG. 6 shows the ability of the MFSO ointment to improve wound healing as measured by mean clinical grading scales for a) redness, b) scab formation, and c) general wound appearance and d) bioinstrumentation measurements of TEWL. The data in the figure are expressed as the mean±SD. There were significant improvements in scab formation (days 4 and 7) and general wound appearance (days 4-14) that were observed with the application of the MFSO containing ointment compared to Neosporin® ointment ($P<0.05$). The average TEWL value was significantly less on day 4 with the use of the MFSO ointment compared to Neosporin® ointment ($P<0.05$). There were no significant differences with regards to the visible signs of redness.

The MFSO ointment demonstrated fast and effective improvements in several wound healing parameters comparable to Neosporin® ointment.

B) MFB Skin Extract Improves Wound Healing

One male subject with a superficial wound of approximately 1-2 cm in length and ¼ cm in depth underwent treatment twice a day with an ointment formulation containing the MFB skin extract. After 20 days, the subject had complete healing of his wound.

Example 16

Anti-Scarring Treatment

MFSO Improves Hypertrophic Scars (Keloids). A pilot clinical study was performed to demonstrate the ability of a MFSO containing gel patch to improve the signs and symptoms of hypertrophic scars (keloids) in post-surgical patients.

3 patients were selected with Mohs post-surgery scars of at least one month duration. These patients had scars that were associated with redness, pruritus, and were approximately 2-3 cm in length and at least ¼ cm in depth. All 3 subjects were evaluated monthly and instructed to apply a MFSO containing gel patch occluding the scar for a period of 12-24 hours daily for 3 months. Efficacy was assessed using mean clinical grading scales for redness, investigator grading of clinical mean scar appearance, and subject questionnaire for intensity of pruritus. Redness grading scale: 0=none, 1=mild, 2=moderate, 3=marked, 4=severe. Scar appearance grading scale: 0=poor, 1=fair, 2=good, 3=very good, 4=excellent. Pruritus grading scale: 0=none, 1=mild, 2=moderate, 3=marked, 4=severe.

The MFSO containing patch was able to improve scar healing in all 3 subjects as measured by investigator assessments using mean clinical grading scales for a) redness, and b) general scar appearance and by subject questionnaires documenting improvement in the severity of pruritus. There were significant improvements in scar redness (months 2 and 3), general scar appearance (month 3), and reduction in scar associated pruritus (months 2 and 3) that were observed with the application of the MFSO containing patch.

Example 17

Anti-Aging Treatment a) MFSO Improves the Visible Signs of Photo-aged Skin and the Appearance of Fine Lines and Wrinkles. A 12-week double blind pilot clinical study was performed to demonstrate a serum containing MFSO had the ability to reverse certain visible clinical signs of aging in subjects with photo-damage involving the skin of the face.

Figure 7:
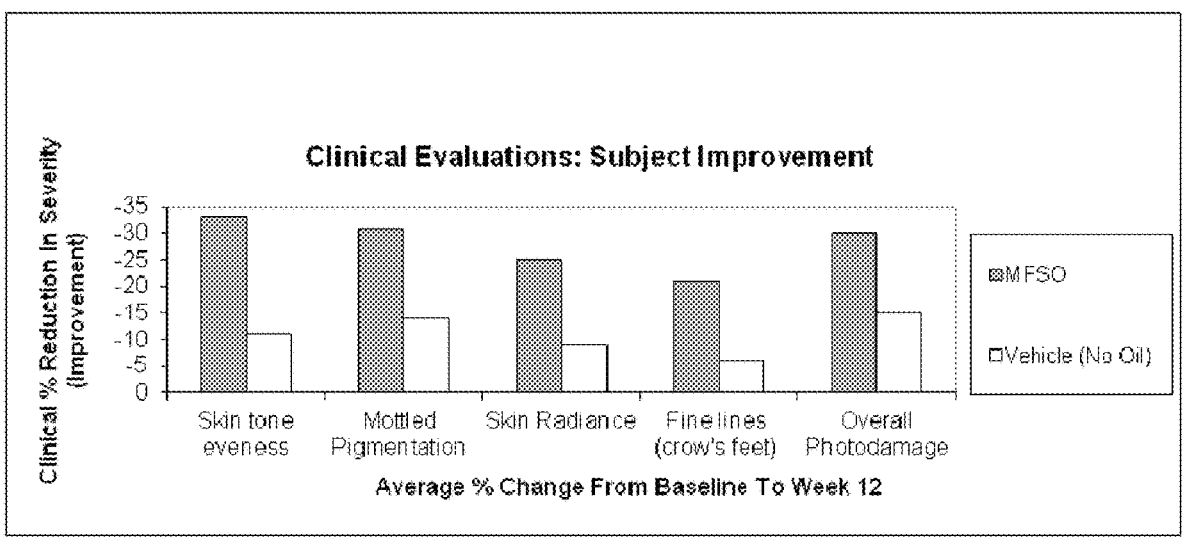
FIG. 7 is a graph depicting that MFSO improves photo-aged skin and the appearance of fine wrinkles in vivo.

A serum containing MFSO was tested (12 women with Fitzpatrick skin type I-III) against its vehicle in a split-face 12-week pilot clinical study. Products were packaged in identical containers, such that investigators and subjects were blinded, with designations on the label for the product to be applied to the right or left side of the face. Each product was applied once daily (after cleansing the face) in the evening to the designated half-side of the face. Subjects were recruited specifically for overall photo-damage consisting of the visible signs of periorbital fine lines (crow's feet wrinkles) and mottled facial pigmentation. The subjects were evaluated at baseline and after 4, and 12 weeks of treatment using a 1-9 scale for photo-aging parameters assessed by a dermatologist, standardized digital photography, and subject self-assessments. Subject improvement was measured as an average % change from baseline (entry) to week 12 at the end of the study. The data that were generated were expressed as the mean±SD. FIG. 7 shows that the MFSO serum performed significantly (P<0.05) better when compared to placebo (vehicle control) on all the clinical anti-aging parameters that were evaluated; mottled pigmentation, crow's feet fine lines (wrinkles) and overall photo-damage.

A serum containing MFSO was well tolerated with no skin irritation and delivered significant clinical and self-perceived improvements and anti-aging benefits.

b) MFB Skin and Pulp Extract Improves the Visible Appearance of Fine Lines.

Two female subjects with a history of photo-damaged skin used a serum containing the MFB skin and pulp extract on the fine lines around their crow's feet daily for 12 weeks. Both subjects claimed that their fine lines showed greater visible improvement compared to the products they were using in the past.

Example 18

Melasma Treatment

MFSO Improves the Visible Signs of Skin Hyperpigmentation (Melasma) on the Face. An open label pilot clinical proof-of-concept study was performed to demonstrate a MFSO containing cream could improve the visible signs of facial hyperpigmentation (Melasma).

5 female subjects were enrolled in a blinded open label study. They were instructed to apply a MFSO cream to one side of their face and the base (cream with no MFSO) to other side of the face on the areas involved with Melasma. The creams (labeled A and B) were consistently applied to the same side of the face every night. After 3 months of use, they were asked to compare the efficacy of both products. A dermatologist, blinded with regards to which side of the face received which treatment, examined each patient during the study and provided assessments using the Average Melasma Area and Severity Index (MASI) evaluations as described (Rendon M, Berneburg M, Arellano I, Picardo M. Treatment of Melasma. J Am Acad Dermatol. 2006 May; 54 (5 Suppl 2):5272-81).

All 5 patients were rated by MSAI scores as improved from baseline on the side of the face that received the MFSO cream while only one subject showed an improvement on the side of the face that received the vehicle cream alone.

This pilot study demonstrated that the MFSO cream was effective in reducing the visible signs of skin hyperpigmentation or Melasma on the skin of the face.

Example 19

Treatment of Inflammatory Conditions

A. MFSO Improves the Visible Signs of Skin Eruptions Associated with the Inflammatory Skin Conditions: Seborrheic Dermatitis, Acne, and Rosacea An open label pilot clinical proof-of-concept study was undertaken to demonstrate a MFSO containing gel could improve the visible signs of skin inflammatory eruptions seen in patients with seborrheic dermatitis (with scalp dandruff), acne, and rosacea.

9 subjects (3 subjects per group; Group 1-seborrheic dermatitis with scalp dandruff; Group 2-inflammatory acne; Group 3-inflammatory rosacea) with active inflammatory skin eruptions were enrolled in a blinded open label study. Patients were selected for entry if they were not using any other therapy for their condition for the prior month. Subjects had to agree to not use other therapies or systemic treatments that could affect the results while on the study. They were instructed to apply a MFSO gel to one side of their face (and scalp if it contained dandruff) and the base (gel with no MFSO) to the other side of the face (and scalp if needed), specifically covering the areas involving the skin eruptions. The gels (labeled A and B) were consistently applied to the same side of the face every morning and night. In subjects with seborrheic dermatitis, the gel was rubbed on the scalp for 5-10 minutes prior to showering. After 4 weeks of use, they were asked to compare the efficacy of both products. A dermatologist, blinded with regards to which side of the face received which treatment, examined each patient during the study and provided assessments.

All 9 subjects were rated by the dermatologist as improved from baseline on the side of the face that received the MFSO gel while only two subjects, one with seborrheic dermatitis and one with acne showed an improvement on the side of the face that received the vehicle gel alone. Of note, all three subjects with rosacea had nearly complete clearing of the sites treated with the MFSO gel. In addition, two subjects showed improvement in scalp dandruff with MFSO.

The pilot study demonstrated that the MFSO gel was effective in reducing the visible signs of skin eruptions associated with inflammatory skin conditions; seborrheic dermatitis, acne and rosacea.

Two subjects, one with acne and the other with seborrheic dermatitis involving the scalp, used a MFB skin extract gel as per the regimen above. Both subjects had significant improvement of their conditions.

B. MFSO Improves the Visible Signs of Skin Eruptions Associated with the Inflammatory Skin Conditions: Psoriasis An open label pilot clinical proof-of-concept study was undertaken to demonstrate a MFSO containing ointment can improve the visible signs of skin inflammatory eruptions seen in patients with mild to moderate psoriasis.

4 subjects with clinically stable inflammatory plaque psoriasis containing scaly eruptions involving greater than 10% of their extremities with a psoriasis area severity index (PAST) of at least 12.0 at screening were enrolled in a blinded open label study. Patients were selected for entry if they were not using any other therapy for psoriasis for the prior month. Subjects had to agree to not use other psoriasis therapies or systemic treatments that could affect the results while on the study. They were instructed to apply a MFSO containing ointment to one side of their extremities and the base (ointment with no MFSO) to the other side of their extremities, specifically covering the areas involving the skin eruptions. The ointments (labeled A and B) were consistently applied to the same side of the extremities every morning and night. After 4 weeks of use, they were asked to compare the efficacy of both products. A dermatologist, blinded with regards to which side of the extremities received which treatment, examined each patient during the study and provided assessments All 4 subjects were rated by the dermatologist as improved from baseline on the side of the extremities that received the MFSO ointment while only one subject showed an improvement on the side that received the vehicle ointment alone.

This pilot study demonstrated that the MFSO ointment was effective in reducing the visible signs of skin eruptions associated with mild to moderate inflammatory plaque psoriasis.

Example 20

Sunscreen Spf-Booster

MFSO boosts the SPF value when combined with a known UVB sunscreen active agent (Table 4).

Formulations containing MFSO and octyl methoxycinnamate (Octinoxate), alone and in combination, were prepared without changing the vehicle base and tested for UVB SPF activity (2 subjects).

In order to demonstrate the contribution of MFSO to the overall SPF, formulations with only one of each of the above sunscreen active agents were first measured. MFSO by itself has no SPF activity. To evaluate for SPF boosting effects of MFSO, a concentration of Octinoxate was selected that gave SPF values that would allow for its efficient absorption and avoid the saturation effect that occurs when higher concentrations of sunscreens are used. It was found that a concentration of Octinoxate (3%) was sufficient to achieve a SPF of 3.

TABLE 4

SPF values

|   | MFSO (%) | Oct (%) | SPF |
|---|---|---|---|
| A | 1 | — | 0 |
| B | 5 | — | 0 |
| C | — | 3 | 3 |
| A + C | 1 | 3 | 4 |
| B + C | 5 | 3 | 5 |

The combination of MFSO with Octinoxate (3%) yielded an SPF of 4 (MFSO 1%) and an SPF of 5 (MFSO 5%) which shows a boosting effect since the resulting SPF was 1-2 units higher than the SPF of 3 that was seen with Octinoxate alone. These results confirm that MFSO imparts a boosting effect by enhancing the SPF activity when combined with formulations containing a known UVB sunscreen active agent.

Example 21

Treatment for Nails

MFSO Improves the Visible Signs of Brittle Nails. An open label pilot clinical proof-of-concept study was undertaken to demonstrate MFSO improves the visible signs and symptoms of brittle nails.

5 subjects were selected with clinical signs and symptoms of brittle fingernails. These subjects had visible signs of nail surface roughness, raggedness and peeling on all nails involving both hands for at least 6 months on no treatment. The subjects were instructed to apply an ointment containing MFSO to all the fingernails on their right hand twice daily for 16 weeks. The subjects were told to continue their normal routines and not use any new nail care product on their left hand. Signs and symptoms were rated by the investigators (physician global assessment improvement score) and by the participants (subjective improvement score) during treatment and 4 weeks after the discontinuation of the use of MFSO.

4 of the 5 patients had significant improvements in their physician global assessment scores at the end of the study and all of the patients subjectively agreed that their fingernails on the right hand had an overall improvement with the use of MFSO when compared to their untreated left hand.

This pilot study demonstrated that MFSO improves the signs and symptoms of brittle fingernails in subjects with brittle nails.

Two subjects with brittle nails used a MFB (5%) skin and pulp extract gel as per the regimen above. Both subjects had significant improvement of their conditions.

Example 22

Treatment for Joints

MFSO improves joint mobility and reduces aching in the joint. An open label pilot clinical pilot clinical study was undertaken to demonstrate the topical application of MFSO on the wrists can reduce wrist joint aches and improve wrist joint mobility in patients with chronic mild carpal tunnel syndrome.

3 subjects (women ages 42-55) were selected with clinical symptoms of bilateral carpal tunnel syndrome lasting for at least 1 month on no treatment. All subjects had chronic mild wrist joint aches not due to a traumatic injury. Each subject applied an ointment containing MFSO twice daily to skin areas overlying their dominant wrist for 4 weeks. The untreated non-dominant wrist served as a control. Subjects were encouraged to continue their normal activities. Clinical signs and symptoms of joint aches were rated by the investigators (physician assessment improvement score) and by the participants (subjective improvement score) at baseline and at the end of treatment. Wrist joint mobility was evaluated using a finger-tapping device (Reitan Neuropsychology Laboratory, Tucson, AZ) as per the instruction manual.

After 4 weeks, all 3 subjects showed improvement in their symptoms of wrist joint aches involving their dominant hand. In contrast, the non-dominant wrist demonstrated no symptomatic improvement and of note, 2 of the 3 patients had a worsening of their wrist joint aches. Finger tapping mobility studies showed that all 3 subjects had an improvement in their index finger tapping rate of their dominant hand (mean improvement of 17%). In contrast, there was no significant improvement in the index finger tapping rate (mean improvement of 3%) when evaluating the non-dominant hand of all 3 subjects.

MFSO reduced joint aches and improved the wrist joint mobility of patients with signs and symptoms of chronic mild carpal tunnel syndrome.

Example 23

Use to Enhance Joint Performance

A) Improvement in Joint Mobility, Stability, and Flexibility

MFSO contained within an elastomer gel wristband device can improve the speed of finger tapping and the stability of fine finger movements in healthy volunteers. In addition, the use of the wristband can increase the flexibility of the hand/finger joints as shown by an improvement in the range of motion (ROM) of the hand/finger joints.

Eight normal male subjects (right-handed & ages 18-55) without a history of joint problems and on no medications or supplements for at least 6 months were selected for study. Subjects were screened and enrolled if they had a measurable difference of greater than 20% in finger tapping (FT) mobility and ROM between their right (dominant/preferred) and left hands. Wrist joint mobility (speed) was evaluated using a modified FT Test App on an iPad device (Sybu Data, Capetown, South Africa) that allowed for the longer tapping duration (3 minutes) as per the instructions of the manufacturer. Finger tapping dexterity and precision were measured using a real world task on a Nokia 3210e phone. Subjects were instructed to dial three land-line phone numbers (11 digits each) sequentially as fast as possible without making any errors. The range of motion of the index finger during its movement (MCP joint movement measured in degrees), was measured using a finger sensor goniometer (Biopac Systems Inc., Goleta, CA) and hand steadiness was tested using the Groove Type Steadiness Tester (Lafayette Instrument Corp., Lafayette, IN) as per the instructions of the manufacturers. All tests were performed in triplicate.

Subjects were divided into 4 groups; Group 1 wore the MFSO wristband, Group 2 wore a grape seed oil wristband, Group 3 wore a wristband with no fruit seed oil and Group 4 wore no wristband. The subjects in the three treatment groups were instructed to wear the wristband on their left wrist (non-dominant/non-preferred hand) for at least 4 hours a day during their normal activities for a total of 4 weeks. The untreated right wrist (dominant/preferred hand) and the subjects who wore no wristband on their left wrist served as controls.

After 4 weeks of use, compared to subjects not wearing a wristband on either hand or those wearing the wristband with no fruit oil, which showed no improvements (defined as less than 10% from baseline), there were improvements from baseline (% difference in performance) in FT speed (18%), FT precision speed (20%), hand steadiness (21%), and ROM at the MCP joint of the index finger (24%) in both groups of subjects wearing the wristbands with the fruit oils. However, the improvements in FT speed, precision, steadiness and ROM were all greatest in the group using the MFSO (average values of 24%, 25%, 28% and 30%, respectively) compared to the group of subjects that wore wristbands containing the grape-seed oil (average values of 12%, 15%, 14%, and 18%, respectively).

B) Improvement in Joint Strength and Endurance

MFSO contained in an elastomer gel wristband device can improve the hand grip strength, finger pinch strength, and the endurance of hand/finger joint movements in healthy volunteers.

Eight normal male subjects (right-handed & ages 18-59) without a history of joint problems and on no medications or supplements for at least 6 months were selected for study. Subjects were screened and enrolled if they had a measurable difference of greater than 20% in Hand Grip Strength and Fatigue testing and index finger FT fatigue testing (after 5 minutes of continuous tapping to evaluate endurance) between their right (dominant/preferred) and left hands. Hand (grip) and finger (pinch) strength and fatigue were measured using a hand dynamometer (Vernier Software and Technology, Beaverton, OR) as per the instructions of the manufacturer. Wrist/finger joint fatigue (endurance) was evaluated using a modified FT Test App that allowed for a measurement of finger tapping over an extended duration of 5-minutes on a keyboard attached to an iPad device (Sybu Data, Capetown, South Africa) as per the instructions of the manufacturer. The modified App was also capable of recording the number of taps for each 30-second interval of the 5-minute test duration, which allowed for additional comparisons of fatigue measurements over time. All tests were performed in triplicate.

Subjects were divided into 4 groups; Group 1 wore the MFSO wristband, Group 2 wore a grape seed oil wristband, Group 3 wore a wristband with no fruit seed oil and Group 4 wore no wristband. The subjects in the three treatment groups were instructed to wear the wristband on their left wrist (non-dominant/non-preferred hand) for at least 4 hours a day during their normal activities for a total of 4 weeks. The untreated right wrist (dominant/preferred hand) and the subjects who wore no wristband on their left wrist served as controls.

After 4 weeks of use, compared to subjects not wearing a wristband on either hand or those wearing the wristband with no fruit oil, which showed no improvements (defined as less than 10% from baseline), there were improvements from baseline (% difference in performance) in hand grip strength (16%), pinch strength (16%), hand grip endurance (18%), and finger tapping endurance (22%) in both groups of subjects wearing the wristbands with the fruit oils. However, the improvements in hand grip strength, pinch strength, hand grip endurance and finger tapping endurance were all greatest in the group using the MFSO (average values of 20%, 22%, 20% and 24%, respectively) compared to the group of subjects that wore wristbands containing the grape-seed oil (average values of 12%, 10%, 16%, and 18%, respectively).

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

Having described the inventions, the following is claimed:

1. A method for treating a condition or disorder affecting hair or skin of an animal in need thereof and caused by or associated with inflammation, the method comprising:
topically applying miracle fruit seed oil extract or a composition comprising miracle fruit seed oil extract to the hair or skin of the animal at an amount effective to inhibit inflammation, promote wound healing, or reduce scar formation, wherein the composition includes at least 1 weight percent miracle fruit seed oil extract and wherein the condition or disorder comprises at least one of atopic dermatitis or psoriasis, acne, rosacea, seborrheic dermatitis, or seborrheic dermatitis with dandruff and the miracle fruit seed oil extract or the composition is administered at an amount effective to treat the atopic dermatitis or psoriasis, acne, rosacea, seborrheic dermatitis, or seborrheic dermatitis with dandruff.

2. The method of claim 1, wherein the condition or disorder comprises at least one of dryness, weathering, aging, or brittleness of hair or skin; skin damage caused by UV radiation; atopic dermatitis or psoriasis; acne; rosacea; seborrheic dermatitis; seborrheic dermatitis with dandruff; scar formation; hair damage caused by dull, frizzed, frayed, frazzled, or tangled hair, or split ends of the hair; breakage of the hair due to a physical, chemical, environmental, or nutritional modality affecting the hair, breakage, loss, or brittleness of hair caused by inflammation of hair follicles; wrinkles or aging of skin caused by inflammation; or undesired pigmentation of skin caused by inflammation.

3. The method of claim 2, wherein the miracle fruit seed oil extract or the composition is applied to hair.

4. The method of claim 3, wherein the condition or disorder is hair breakage, loss, damage or brittleness caused by inflammation of hair follicles.

5. The method of claim 1, wherein the miracle fruit seed oil extract or the composition is topically applied to the skin at an amount effective to change skin pigmentation.

6. The method of claim 1, wherein the miracle fruit seed oil extract or the composition is topically applied to the skin at an amount effect to moisturize the skin.

7. The method of claim 1, wherein the miracle fruit seed oil extract or composition is topically applied to the skin at an amount effective to lubricate the skin.

8. The method of claim 1, wherein the miracle fruit seed oil extract or the composition is topically applied to the skin at an amount effective to protect the skin from irritation.

9. The method of claim 1, wherein the inflammation is caused by or associated with a microbe.

10. The method of claim 1, wherein the miracle fruit seed oil extract or the composition is topically applied to the skin at an amount effective to promote wound healing or inhibit scar formation.

11. The method of claim 1, wherein the miracle fruit seed oil extract or the composition is topically applied to skin proximate a joint or a joint of the animal at an amount effective to improve at least one of joint mobility, dexterity, strength, stability, endurance or flexibility.

12. The method of claim 1, wherein the miracle fruit seed oil extract or the composition is topically applied to skin proximate a muscle of the animal at an amount effective to improve at least one of muscle weakness and fatigue.

13. The method of claim 1, wherein the composition further comprises at least one of a pharmaceutically or cosmetically acceptable additive, excipient, or carrier that is exogenous to miracle fruit and facilitates topical delivery of the oil extract.

14. The method of claim 1, wherein the miracle fruit seed oil extract is a cold or hot pressed, solvent, or supercritical fluid oil extract from seed of the miracle fruit berry.

15. The method of claim 1, wherein the composition is in the form of a lotion, gel, liquid, oil, foam, paste, spray, cream, ointment, powder, suppository, troche, patch, strip, film, or emulsion.

16. The method of claim 1, wherein the miracle fruit seed oil extract comprises about 43 wt. % to about 46 wt. % palmitic acid, about 32 wt. % to about 34 wt. % oleic acid, and about 18 wt. % to about 21 wt. % linoleic acid.

17. The method of claim 1, wherein the miracle fruit seed oil extract further comprises about 5 wt. % to about 7 wt. % stearic acid and about 1 wt. % to about 2 wt. % myristic acid.

18. The method of claim 1, wherein the miracle fruit seed oil extract further comprises at least one hydrocarbon, triterpene alcohol, low molecular weight alcohol, or sterol.

19. A method for treating a condition or disorder affecting hair or skin of an animal in need thereof and caused by or associated with inflammation, the method comprising:
topically applying miracle fruit seed oil extract and/or a composition comprising miracle fruit seed oil extract to the hair or skin of the animal at an amount effective to treat said condition or disorder, wherein the composition includes at least 5 weight percent miracle fruit seed oil extract and wherein the condition or disorder comprises at least one of atopic dermatitis or psoriasis, acne, rosacea, seborrheic dermatitis, or seborrheic dermatitis with dandruff and the miracle fruit seed oil extract or the composition is administered at an amount effective to treat the atopic dermatitis or psoriasis, acne, rosacea, seborrheic dermatitis, or seborrheic dermatitis with dandruff.

* * * * *